United States Patent
He et al.

(10) Patent No.: US 11,852,624 B1
(45) Date of Patent: Dec. 26, 2023

(54) METHOD AND APPARATUS FOR SMALL MOLECULE DETECTION BY NANOPIPETTE

(71) Applicants: Jin He, Miami, FL (US); Santosh Khatri, Miami, FL (US); Popular Pandey, Miami, FL (US)

(72) Inventors: Jin He, Miami, FL (US); Santosh Khatri, Miami, FL (US); Popular Pandey, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/103,746

(22) Filed: Jan. 31, 2023

(51) Int. Cl.
| | |
|---|---|
| *G01N 27/327* | (2006.01) |
| *G01N 33/487* | (2006.01) |
| *G01N 27/447* | (2006.01) |
| *G01Q 60/44* | (2010.01) |

(52) U.S. Cl.
CPC . *G01N 33/48721* (2013.01); *G01N 27/44791* (2013.01); *G01Q 60/44* (2013.01)

(58) Field of Classification Search
CPC ................................................ G01N 33/48721
See application file for complete search history.

(56) References Cited

U.S. PATENT DOCUMENTS

| | | | |
|---|---|---|---|
| 9,766,204 B2 | 9/2017 | Karhanek et al. | |
| 10,513,434 B2 | 12/2019 | Seger et al. | |
| 2009/0136958 A1* | 5/2009 | Gershow .............. | C12Q 1/6825 977/924 |

OTHER PUBLICATIONS

Sulaiman et al., "Chemically Modified Hydrogel-Filled Nanopores: A Tunable Platform for Single-Molecule Sensing," Nano Lett. 2018, 18, 6084-6093, including supplementary information (Year: 2018).*
Tiwara et al., "Quantitative study of protein-protein interactions by quartz nanopipettes," Nanoscale, 2014, 6, 10255-10263 (Year: 2014).*
The dissertation of Ch Chang Chau entitled, "Single Molecule Delivery and Detection into Crowded Environment with a Solid-State Nanopore," The University of Leeds—School of Molecular and Cellular Biology, Jun. 2021 (Year: 2021).*
Sean et al., "Langevin dynamics simulations of driven polymer translocation into a cross-linked gel," Electrophoresis 2017. 38, 653-658 (Year: 2017).*

(Continued)

*Primary Examiner* — Alexander S Noguerola
(74) *Attorney, Agent, or Firm* — SALIWANCHIK, LLOYD & EISENSCHENK

(57) ABSTRACT

A system, apparatus, device and/or method for electrical label-free detection of single molecule via a glass or quartz nanopipette biosensor, one type of solid state nanopore biosensor based on resistive pulse measurements, are provided. The method of the subject invention effectively slows down the motion of biomolecules and concentrates them at the nanopipette tip. By driving biomolecules to come out of the nanopipette barrel and move in the fibrin hydrogel, unprecedented sensitivity using the typical size nanopipettes can be achieved. Small molecules such as doxorubicin, ATP, GTP, and short peptides can be easily detected with very high event rate, which greatly reduces the fabrication and measurement difficulties and open opportunities for various new applications for nanopipette biosensors.

19 Claims, 10 Drawing Sheets

(56) References Cited

OTHER PUBLICATIONS

Waugh et al., "Interfacing solid-state nanopores with gel media to slow DNA translocations," Electrophoresis 2015, 36, 1759-1767 (Year: 2015).*
Jia et al., Identification of Single-Molecule Catecholamine Enantiomers Using a Programmable Nanopore, ACS Nano 2022, 16, 6615-6624 (Year: 2022).*
Boersma et al., "Continuous Stochastic Detection of Amino Acid Enantiomers with a Protein Nanopore **," Angew. Chem. Int. Ed. 2012, 51, 9606-9609 (Year: 2012).*
Zhao et al., "Single molecule Spectroscopy of Amino Acids and Peptides by Recognition Tunneling," Nat Nanotechnol. Jun. 2014; 9(6), 466-473 (Year: 2014).*
Bulbul, Gonca et al. "Nanopipettes as Monitoring Probes for the Single Living Cell: State of the Art and Future Directions in Molecular Biology." Cells 7(6): 1-21, Jun. 6, 2018.
Cadinu, Paolo et al. "Double Barrel Nanopores as a New Tool for Controlling Single-Molecule Transport." Nano Letters 18(4):2738-2745, (Year: 2018).
Cadinu, Paolo et al. "Individually Adressable Multi-nanopores for Single-Molecule Targeted Operations." Nano Letters 20(3):2012-2019, (Year:2020).
Cadinu, Paolo et al. "Single Molecule Trapping and Sensing Using Dual Nanopores Separated by a Zeptoliter Nanobridge." Nano Letters 17(10):6376-6384, (Year: 2017).
Li, Zi-Yuan et al. "High-Preservation Single-Cell Operation through a Photo-responsive Hydrogel-Nanopipette System." Angew. Chem. Int. Ed. 60(10):5157-5161, (Year: 2021).
Sulaiman, Dana Al et al. "Chemically Modified Hydrogel-Filled Nanopores: A tunable Platform for Single-Molecule Sensing." Nano Letters 18(9):6084-6093, (Year: 2018).

* cited by examiner

FIG. 3A
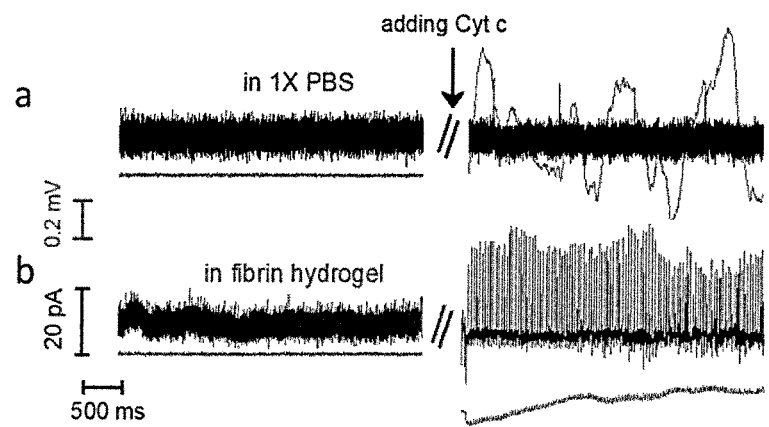
FIG. 3B
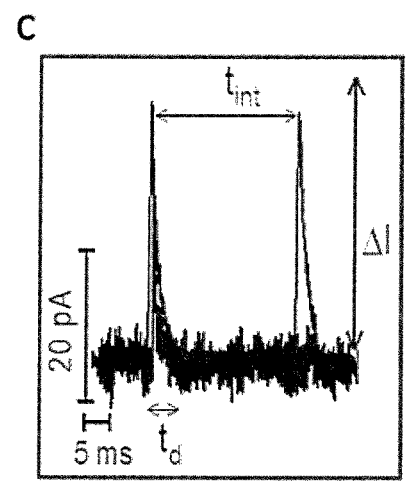
FIG. 3C

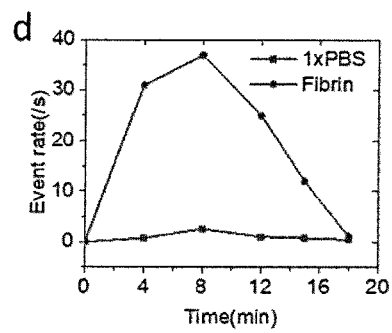
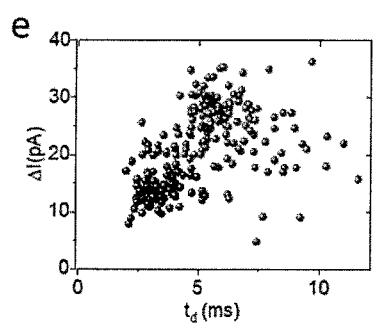
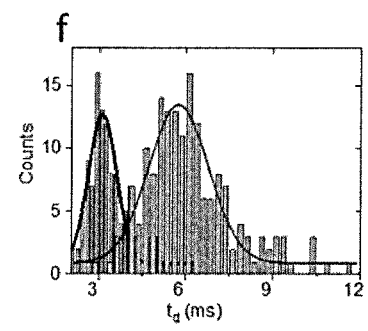
FIG. 3D  FIG. 3E  FIG. 3F
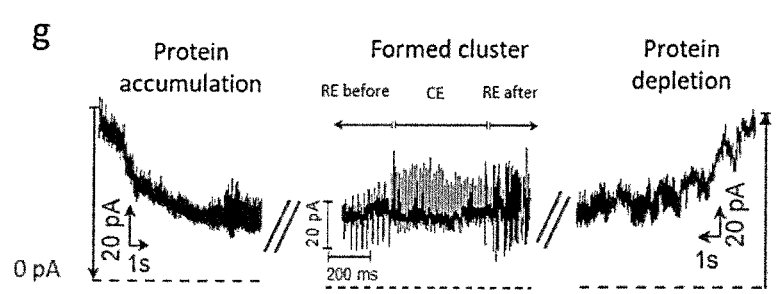
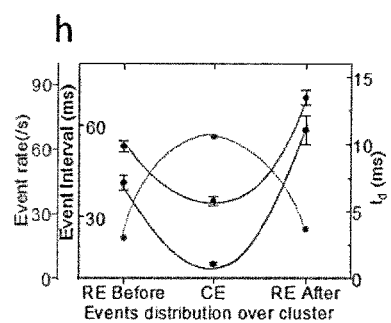
FIG. 3G  FIG. 3H

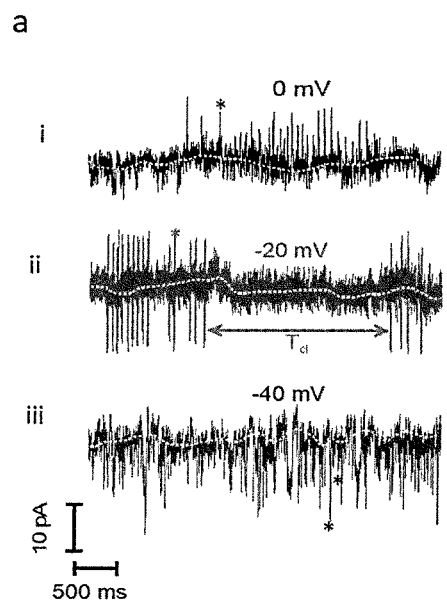
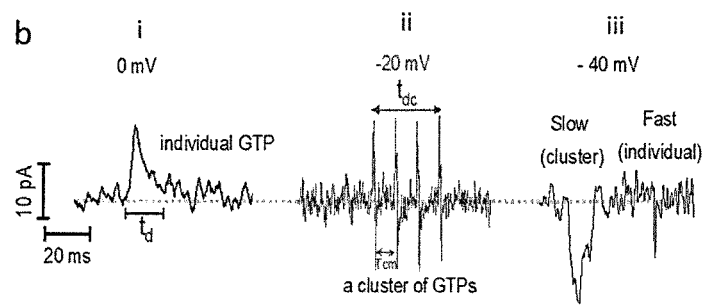
FIG. 7A  FIG. 7B
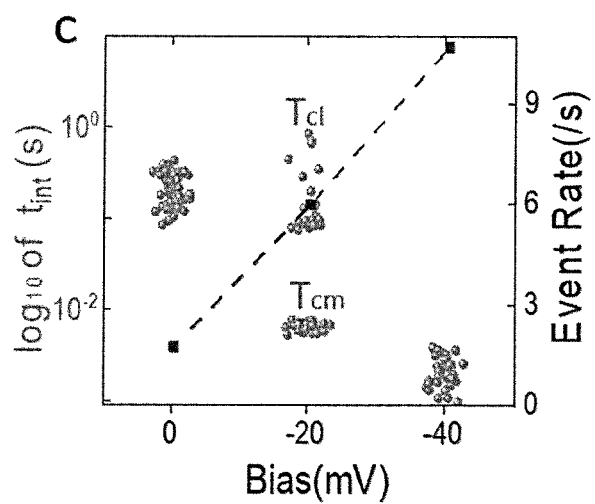
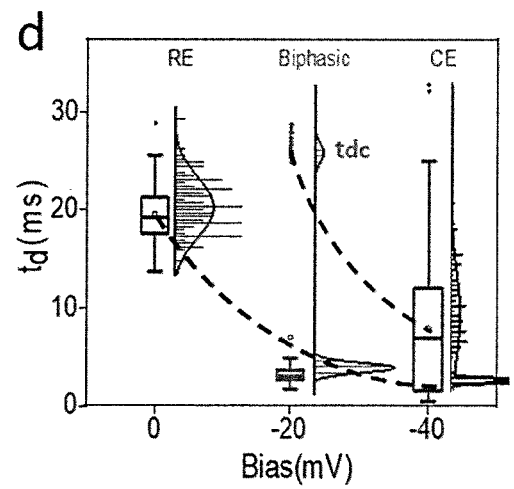
FIG. 7C  FIG. 7D

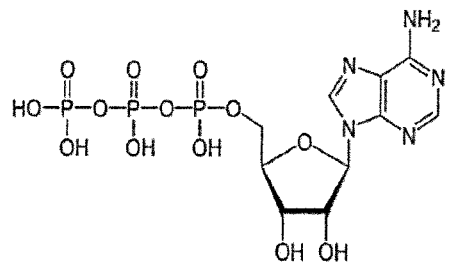
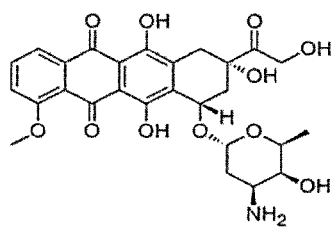
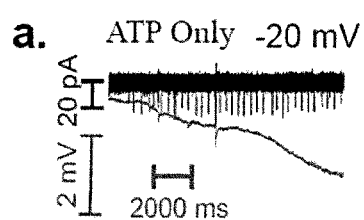
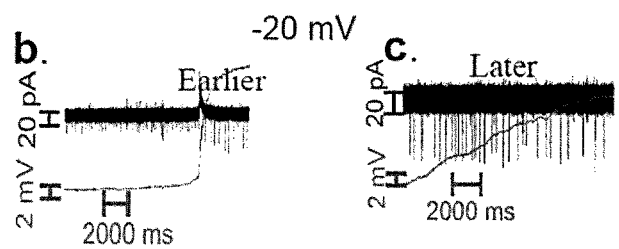
FIG. 8A  FIG. 8B  FIG. 8C
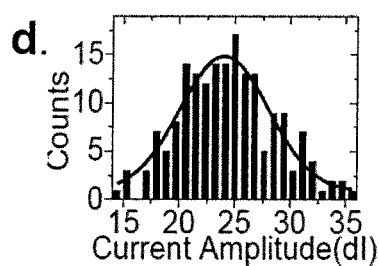
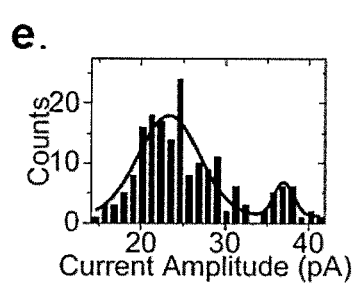
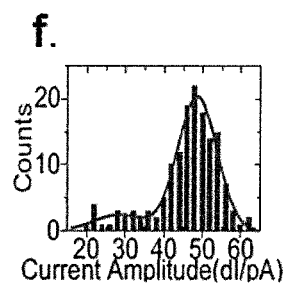
FIG. 8D  FIG. 8E  FIG. 8F

METHOD AND APPARATUS FOR SMALL MOLECULE DETECTION BY NANOPIPETTE

GOVERNMENT SUPPORT

This invention was made with government support under CBET1454544 awarded by the National Science Foundation. The government has certain rights in the invention.

BACKGROUND OF THE INVENTION

A nanometer-sized hole, called a Nanopore, can serve as an electrical sensor to detect various biomolecules to obtain information about their physical and chemical properties that can be viewed as a Coulter counter in the nanoscale range. The nanopore method has achieved great success in DNA sequencing. Nanopores have also been used to detect other biomolecules such as RNA and proteins. Glass or quartz nanopipettes, as a subtype of the solid-state nanopore, have also been increasingly used for DNA and protein detection. However, there is still a major hurdle in applying nanopipette for the detection of various biomolecules, especially smaller proteins (100 amino acids or less), short peptides (50 amino acids or less), small molecules such as Adenosine triphosphate (ATP) and Guanosine triphosphate (GTP), and drug molecules such as Doxorubicin.

Different from the conventional solid-state nanopores fabricated on ultrathin SiN or $SiO_2$ membranes by focused electron or ion beams, nanopipettes can be cheaply, conveniently, and quickly prepared by a commercial pipette puller. However, compared with solid-state nanopores, the nanopipette suffers from larger nanopore size variation, and, thus, it is difficult to reliably produce a nanopore with a size less than 10 nm.

Nanopore sensing is mainly based on the measurement of resistive pulses due to the volume exclusion of the target molecule in the nanopore sensing volume. Therefore, the lack of size control at the sub-10 nm resolution severely limits the application of nanopipettes for small molecule detection and analysis. Small biomolecules with a size less than a few nanometers typically move too fast to be reliably detected by ionic current when they are passing through the orifice of the nanopipette. Therefore, the nanopipette often lacks the sensitivity to detect small molecules with a size less than a few nanometers due to the very low signal-to-noise ratio and detection rate for biomolecules.

Different from most flat thin-film based solid-state nanopores, the nanopore of the nanopipette is connected to a long nanochannel, which provides a bigger space for the confinement effect. Many studies have demonstrated that nanoconfinement is critical for noise reduction and signal amplification of single-entity electrochemistry (SEE) techniques and the key to push the sensitivity to reach the single-molecule level.

Dielectrophoresis (DEP) has been used to concentrate synthetic nanoparticles near the nanopipette tip, which introduces self-crowding and leading to an enhancement in the signal-to-noise ratio and the event rate. However, the DEP method is not effective for small biomolecules. Further, the addition of crowding agents is still not sufficient to enrich small biomolecules near the nanopore and reach the desired sensitivity of small biomolecules using nanopipettes with a pore size of 10 nm or more.

Therefore, there is a need to develop materials and methods to maximize the nanoconfinement effect of a nanopipette tip for ultrasensitive and highly effective detection of biomolecules, such as proteins and peptides, at a single molecule level, in particular, when using a nanopipette with a pore size larger than 10 nm.

BRIEF SUMMARY OF THE INVENTION

The subject invention provides systems, apparatuses, devices, and methods for enhanced, label-free detections and analyses of biomolecules such as proteins, peptides, and other small molecules, and their dynamic interactions. The system can be utilized as a portable and point-of-care device. This technology can be used in the fields of, for example, the rapid developed precision medicine and personalized medicine. The methods of the subject invention are easy to perform, highly sensitive and cost-effective.

In one embodiment, the systems, apparatuses, devices and methods relate to the field of detection of biomolecules within a sample, such as testing for the presence and/or concentration of one or more proteins within a sample solution for the purposes of screening for diseases and conditions. The systems, apparatuses, devices and methods of the subject invention provide fewer contamination issues, less electrical noise and a larger detection range, and can probe various biological entities at a single-entity level.

In one embodiment, the system, apparatus and/or device comprises a nanopipette that can be filled with a solution comprising one or more biomolecules; a working electrode inserted in the nanopipette (i.e., cis side); a crowding agent (e.g., various types of hydrogel or the mixture of hydrogels or high molecular weight polymer like PEG 20 k) placed at the trans side (outside) of the nanopore of the nanopipette; and a reference electrode dipped in the crowding agent (e.g., various types of hydrogel or the mixture of hydrogels or high molecular weight polymer like PEG 20 k), wherein a bias can be optionally applied between the working electrode and the reference electrode.

In one embodiment, the method and system disclosed herein relate to rapid detection and precise quantification of molecular biomarkers in human blood, e.g., diluted human blood, and in other types of body fluids, including, serum, plasma, semen, saliva, sweat, urine, and tear.

Advantageously, the subject invention overcomes the major limitations in spatial and time resolutions of using a nanopipette for small molecule detection. The method of the subject invention can achieve ultrahigh sensitivity, signal-to-noise ratio (SNR) and event rate for the detection of small molecules down to 1 nm size and below 1 kDa molecular weight without pushing the size limit of nanopipette nanopore and the time resolution of the current amplifier.

The subject invention can be employed to improve the nanoconfinement effect of a nanopipette tip to induce controllable crowding of small biomolecules near the nanopipette nanopore. One scheme of the design is shown in FIG. 1. In one embodiment, the nanopipette has a long taper tip. To reach the nanopore orifice, the biomolecules need to pass a long nanochannel (several microns), which provides strong nanoconfinement. The speed of biomolecules can be effectively slowed when they reach the orifice. Fibrin hydrogel can be added outside the nanopipette tip. With the fibrin hydrogel surrounding the orifice, the speed of the translocating biomolecules, especially for small ones, is further reduced.

Benefiting from the dual slowing mechanism, the biomolecules can be effectively concentrated near the tip. The self-crowding of biomolecules near the tip can improve both the event rate and signal-to-noise ratio for single-molecule detection of small biomolecules. Therefore, this method can achieve ultrahigh sensitivity for label-dree small molecule counting and detection under physiological conditions at the ambient environment.

In one embodiment, the subject invention provides a method for enhanced, label-free single molecule detection in a sample, wherein the method comprises contacting the sample with a system comprising a nanopipette disposed with an electrode and dipped in a crowding agent (e.g., various types of hydrogel or the mixture of hydrogels or high molecular weight polymer like PEG 20 k); and measuring an electrical signal due to translocation of individual molecules through a nanopore of the nanopipette, wherein contacting the sample with the system comprises introducing the sample in an open barrel of the nanopipette. The system can further comprise a reference electrode dipped in the crowding agent (e.g., various types of hydrogel or the mixture of hydrogels or high molecular weight polymer like PEG 20 k). In one embodiment, the method further comprises applying a bias in the system.

The intermolecular interaction between biomolecules is very important and complex. These interactions include processes such as DNA replication, DNA transcriptions, and catalytic metabolism. The subject invention can be used to investigate the interaction mechanism of biomolecules, such as dimmer formation of peptides, protein-protein interactions, hydrogen bonding interactions between DNA nucleotides and the formation of G-quadruplex (G4) of GTP.

In one embodiment, the subject invention provides a method for detecting intermolecular interactions between small biomolecules and determining the stereochemistry of formed complex, the method comprising introducing a sample solution containing the small biomolecules into an open barrel of a nanopipette, the nanopipette having a nanopore at the tip and a working electrode disposed within the sample solution containing the small biomolecules; dipping the tip of the nanopipette in a hydrogel; placing a reference electrode in the hydrogel; and measuring an electrical signal.

In one embodiment, the method further comprises applying a bias between the working electrode and the reference electrode. When a bias is applied from the backend of the nanopipette, the molecules are pressed into the confined space of the nanopipette tip. Due to the crowded space and/or the external electric force, the molecules can interact by overcoming the electrostatic repulsion and steric hindrance. Also, the molecules are effectively concentrated and confined at the tip, leading to enhanced interactions and complex formations In a preferred embodiment, the hydrogel is an ion and small molecule permeable porous hydrogel. In a specific embodiment, the hydrogel is fibrin.

In certain embodiments, the nanopipette is a single, double, or multi-barreled nanopipette.

In one embodiment, the sample solution is a diluted biological sample from a subject.

In one embodiment, the subject invention provides a method for slowing down the translocation of small biomolecules through the nanopore of a nanopipette, the method comprising introducing a sample solution containing the small biomolecules into an open barrel of a nanopipette, the nanopipette having a nanopore at the tip and a working electrode disposed within the sample solution containing the small biomolecules; dipping the tip of the nanopipette in a fibrin hydrogel; placing a reference electrode in the fibrin hydrogel; and measuring an electrical signal upon translocation of the small biomolecules through the nanopore of the nanopipette. Specifically, the small biomolecules are effectively slowed down from the self-crowding of small biomolecules at the tip.

In specific embodiments, the small biomolecules are selected from, for example, ATP, ADP, AMP, GTP, GDP, GMP, heme peptide microperoxidase-11 (MP-11), antibacterial peptide nisin, cytochrome-c, insulin, high-mobility group AT-hook 2 (HMGA21 and lysozyme. For comparison, larger biomolecules are selected from, for example, hemoglobin, IgG, bovine serum albumin, and ferritin.

BRIEF DESCRIPTION OF THE DRAWINGS

FIGS. 3A-3H. The measurement of cyt c. (3A-3B) the typical i-t (black) and v-t (gray) traces before (left) and after (right) adding cyt c with 1×PBS (3A) or fibrin hydrogel (3B) at the trans side. (3C) The zoom-in current spikes in 1×PBS (black) or in fibrin hydrogel (dark gray). The separation between two current spike peaks was defined by event interval ($t_{int}$) (3D) The event rate (/s) change over time in 1×PBS and fibrin hydrogel. To calculate the event rate, the number of events in a cluster were counted at time and were divided by time duration of cluster. (3E) The scatter plots of the current amplitude vs. the dwell time of the current spikes detected in 1×PBS (black, n=145) and fibrin hydrogel (dark gray, n=168). (3F) Histograms of the dwell time in 1×PBS and hydrogel. All the data are collected at zero $V_{pore}$. (3G) The oval current trace change during the enrichment. Zoomed-in trace at the middle show the dynamics of event distribution (3H) The statistics of current spikes in (3H).

FIGS. 7A-7D. G-Quadruplex formation in nano-confined region in response to negative bias. (7A) the i-t traces of GTP translocation at different Vpore bias. (7B) zoomed in trace of individual current spikes. (7C) the event rate and molecular separation at different Vpore bias. (7D) the box normal plot of GTP dwell time at different Vpore bias. The dash lines are for eye guides.

FIGS. 8A-8G. (8A) Ionic current and potential time trace on delivering 100 pM ATP into the hydrogel at −20 my bias. (8B) Ionic current change after 100 pM doxorubicin introduced in the solution containing 100 pM ATP (1:1 by volume). (8C) Ionic current and potential trace of ATP and Doxorubicin complex. (8D) Distribution of current amplitude (dI) of ATP alone. (8E, and 8F) Distribution of current amplitude of ATP-doxorubicin complex. (8G) scatter plot of current amplitude vs. dwell time ATP alone and ATP-Dox complex.

DETAILED DESCRIPTION OF THE INVENTION

Figure 1A:
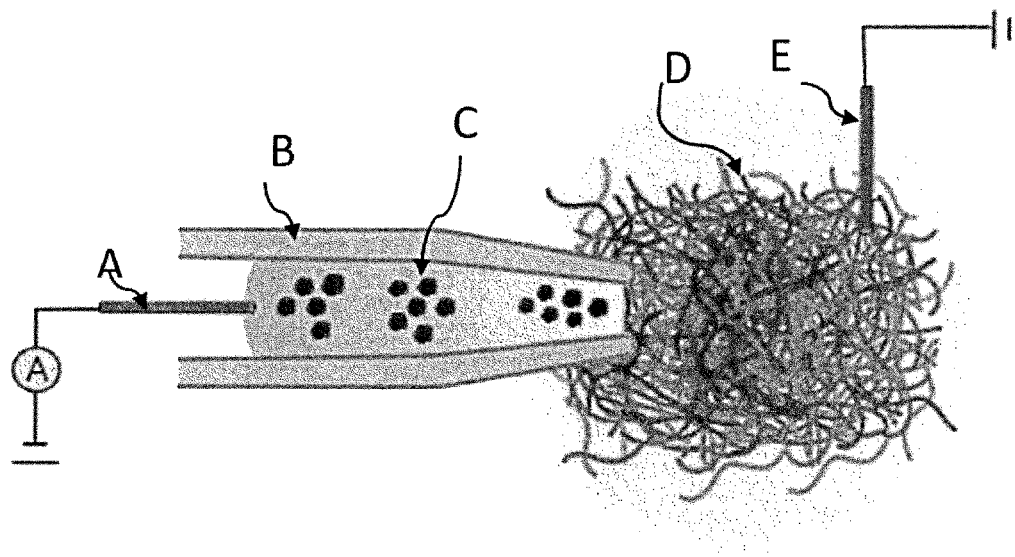
FIGS. 1A-1E. A schematic representation of the set up (1A-1C) and the 2D (1D) and 3D (1E) fibrin networks.

The subject invention provides systems, apparatuses, devices, and methods for label-free detections and analyses of biomolecules such as proteins, peptides, and other small molecules, and their dynamic interactions. The system can be utilized as a portable and point-of-care device. This technology can be used in the fields of, for example, the rapid developed precision medicine and personalized medicine.

In one embodiment, the systems, apparatuses, devices and methods relate to the field of detection of biomolecules within a sample, such as testing for the presence and/or concentration of one or more proteins within a sample solution for the purposes of screening for diseases and conditions.

In one embodiment, the systems, apparatuses, and devices are directed to nanopipettes containing biomolecules that can be crowded at the tip of the nanopipette for ultrasensitive detection of such biomolecules upon their translocation through the nanopore of the nanopipette.

The nanopipette is a subpart of solid state nanopore that mimicks an ion-channel. The nanopipette is a hollow self-supporting, inert, non-biological structure with a conical tip opening of nanoscale, e.g., 0.05 nm to about 500 nm, preferably, 0.05 nm to about 200 nm, more preferably, 0.05 nm to about 50 nm. The hollow structure may be, for example, glass or quartz and is suitable for holding inside of it, or on one side of the nanopore, a fluid that is passed through the nanopore opening. The interior of the nanopipette is selected or modified to reduce nonspecific binding of analyte. The interior is sized to allow insertion of an electrode that contacts solution in the nanopipette.

The nanopipette can be conveniently and cheaply prepared from capillaries by, for example, a commercially-available laser pipette puller (e.g., Sutter Instrument P-2000). The relatively simple, inexpensive and accurate fabrication of nanopipette has played a key role in its widespread application for detection of small biomolecule, nano injection, nano-biopsy, drug delivery and aspiration of biomolecules from cell.

A "multi-barreled nanopipette" is a nanopipette that has two or more parallel bores that typically share a common wall. The bores are co-axial, typically radially spaced, but may be concentric. They may be fabricated from multi-barrel capillary tubes, which are commercially available.

In one embodiment, the system, apparatus and/or device comprises a nanopipette; a working electrode inserted in the nanopipette; a crowding agent (e.g., hydrogel or polymer) placed at the trans side (outside) of the nanopore of the nanopipette; and a reference electrode dipped in the crowding agent (e.g., hydrogel or polymer), wherein a bias can be optionally applied between the working electrode and the reference electrode.

The subject invention leverages the superior confinement effect of the nanopipette to achieve high sensitivity detection of small molecules. One scheme of the approach is illustrated in FIG. 1. By loading the molecule solution from the back end of the nanopipette nanopore barrel, the molecules are forced to diffuse or drift toward the tip orifice. The nanoconfinement slows the motion of small biomolecules until they are enriched at the tip before their translocation.

Two aspects of the design can advantageously help to achieve this goal: 1) a long taper tip (e.g., several microns) geometry further enhances the nanoconfinement effect; 2) an ion and small molecule permeable hydrogel (e.g., fibrin) hinders the exit of small molecules. This combines the "hard" confinement from the nanopipette long tip at the cis side and the "soft" confinement from the hydrogel at the trans side.

The fibrin hydrogel (the mixture of fibrinogen and thrombin in the ratio of, for example, 3:1) is made up of nanometer size fibers. Due to the porous structure, the mobility of ions (such as sodium, potassium and chloride ions) is still high inside the hydrogel and the resistance of the fibrin hydrogel is smaller than the nanopore resistance. In contrast, the effective mobility of small biomolecules is further slowed due to the interaction and hindrances from the fibrin fibers. In addition, the slowed ion and molecule movement can lead to a concentration polarization near the tip, further slowing down the motion of biomolecules and amplify the ionic signal. Therefore, the biomolecules often reside longer in the sensing zone near the orifice.

By applying these two design elements in the measurements, unprecedented high sensitivity and event rate can be achieved for small molecules, including molecules less than 2 nm. For example, even small molecules (such as microperoxidase (MP-11), insulin, adenosine triphosphate (ATP) and guanosine-5'-triphosphate (GTP)) can be preconcentrated and confined near the tip in a controlled fashion.

Due to the enrichment, small molecules can be detected easily with high SNR and high event rate even when the nanopore size is 5-10 times bigger than the molecule. Such high small molecule sensitivity has never before been accomplished using a nanopipette. The advantages of the subject invention include: 1) the enriched molecules can reduce the effective nanopore sensing volume, boosting the volume exclusion based nanopore sensitivity and relaxing the size requirement for the nanopore; 2) the self-crowding of small molecules near the tip slows down the motion of molecules and reduces their thermal and conformational fluctuations, greatly improving the SNR of signals at the sub-millisecond time resolution; 3) the enrichment leads to a high detection rate even for low concentration (e.g., sub pM) samples; 4) the enrichment at the tip facilitates the study of intermolecular interactions and reactions between small molecules in a confined and crowded environment at the single-molecule level.

The method of the subject invention is innovative. Firstly, the self-crowding of targeting molecules in the sensing volume is often regarded as a negative effect and should be avoided. To acquire clean signals, most single-molecule techniques, including nanopore sensing, prefer to conduct the measurement with only one or a few target molecules in the sensing volume. Although the nanopore sensing zone can also be crowded by macromolecules, only the self-crowding by small molecules could generate superior crowding effects to enhance the volume exclusion of small molecules, leading to high sensitivity, SNR and event rate for small molecule detection.

Secondly, the potential detriment of flooding the confined sensing volume with target molecules is the more complicated ionic signals induced by the dynamic spatiotemporal changes in ion and molecule concentration and electrostatic potentials. However, these complexed signals also carry rich information that provides an opportunity for new sensing mechanisms. Thirdly, this approach provides exciting opportunities to study intermolecular interactions and reactions between label-free small soluble molecules in a confined space with controllable crowding effect, which is still very challenging to be achieved by current single-molecule techniques. A range of new biophysical questions regarding small molecule interactions under physiological conditions can be studied using the approach.

Figures 1B, 1C:
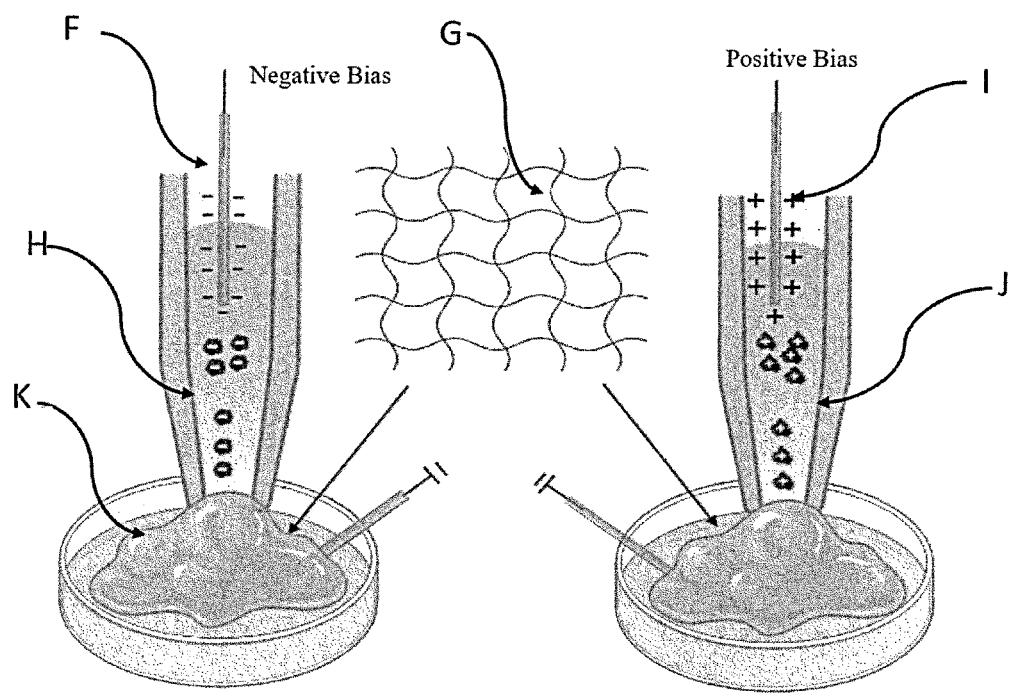
Figure 1D:
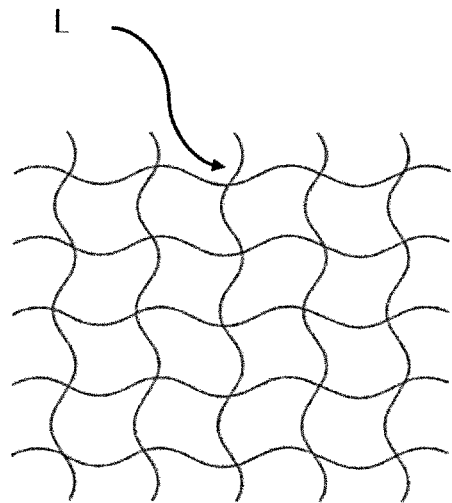
Figure 1E:
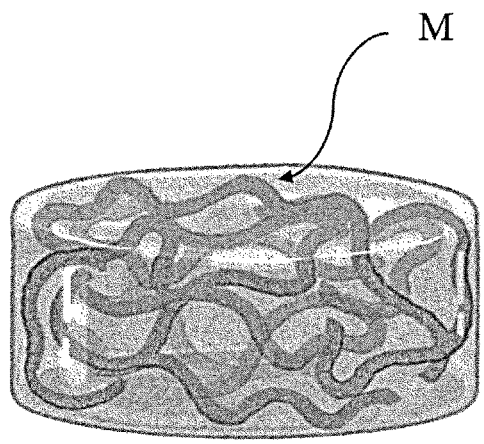

In specific embodiments, the system, apparatus and/or device is illustrated by schematics illustrations, which are not drawn to scale. FIG. 1 illustrates the schematic diagram of one embodiment of the system, apparatus and/or device. A needle shaped nanopipette B is filled with the molecules C inside, which are loaded from the backend of the nanopipette barrel by a syringe with a micron size needle. For small biomolecules, they can quickly move to the orifice by diffusion due their high mobility. For larger biomolecules or nanoparticles (>10 nm), a bias can be applied to drive them to the tip. The Ag/AgCl electrode A is inserted into the solution inside the nanopipette barrel. Bias is applied through the electrode A inside the nanopipette barrel. The nanopipette tip is dipped into the fibrin hydrogel D. The fibrin hydrogel is prepared by mixing fibrinogen and thrombin in the volume ratio 3:1 in 1×PBS (pH~7.4). The formed fibrin hydrogel is immersed in 1×PBS solution G. The grounded Ag/AgCl reference electrode E is also dipped in the fibrin hydrogel. The bias is applied between the electrodes A and E. The two-dimensional schematic drawing of fibrin hydrogel is illustrated in FIGS. 1B and 1C. The 2D and 3D fibrin networks are illustrated by schematic illustrations in FIGS. 1D and 1E, respectively.

In one embodiment, the system, apparatus and/or device comprises a double-barrel nanopipette sensor comprising a double-barrel nanopipette connecting two compartments or reservoirs: first and second compartments or reservoirs, each with its own electrode, a first electrode and a second electrode.

In a preferred embodiment, the first electrode and the second electrode are preferably Ag/AgCl electrodes. The disclosed nanopipette biosensor allows for the quick, low-cost quantification of biomolecules within a given sample.

In one embodiment, the nanopipette has a tapered tip. One important advantage of the nanopipette is that it can be made cheaply and reproducibly, with a few tens of nanometer resolution, from, for example, glass or quartz capillary tubes. It is highly versatile in application and fabrication. For example, the nanopipette can be used as a nanopore sensor for chemical and biological sensing and electrophysiological applications. Owing to its tip geometry, the nanopipette can also be developed as a scanning probe for scanning ion conductance microscopy (SICM) and scanning electrochemical microscopy (SECM).

The term "quartz" means a fused silica or amorphous quartz, or crystalline quartz. Ceramics and glass ceramics and borosilicate glasses may also be utilized. The term "quartz" encompasses that specific material as well as applicable ceramics, glass ceramics or borosilicate glasses. Various types of glass or quartz may be used in the present nanopipette fabrication. A primary consideration is the ability of the material to be drawn to a narrow diameter opening. The preferred nanopipette material consists essentially of silicon dioxide, as included in the form of various types of glass and quartz.

In a specific embodiment, a double-barrel nanopipette is fabricated from theta micropipettes. One barrel is converted to a nanoelectrode by filling the tip of the barrel with conductive materials, such as pyrolytic carbon, copper, graphite, titanium, brass, palladium, silver, platinum, and/or gold. The other barrel remains open at the tip and can be used as a nanopore. The nanoelectrode can be made by various methods known in the art. The open barrel is suitable for holding inside of it a fluid that can be passed through the nanopore at the tip opening. The two barrels are separated by a thin wall, e.g., a quartz wall.

In one embodiment, the first compartment or reservoir is the bath compartment or reservoir containing a crowding agent (e.g., hydrogel or polymer). The second compartment or reservoir receives a solution that fills the open barrel of the nanopipette. The first and second compartments or reservoirs are in fluid communication via the nanopore at the tip of the nanopipette. Preferably, the solution that fills the open barrel of the nanopipette is an electrolyte.

In one embodiment, the double-barrel nanopipette comprises a nanopore and a nanoelectrode at the tip. The nanopore and the nanoelectrode are next to each other. In one embodiment, the nanoelectrode is a stable nanoscale conductive electrode, such as a carbon, gold, platinum or palladium nanoelectrode. In a preferred embodiment, the nanoelectrode is a CNE made by deposition of pyrolyzed carbon in a quartz nanopipette. The final CNE geometry can be controlled by the flow speed/pressure of butane (carbon source) and argon (protective gas) during carbon deposition.

In one embodiment, the first electrode in the first compartment is a reference electrode to the second electrode and the nanoelectrode. When an electric potential is applied to the sensor via the first and second electrodes in the first and second compartments, an ionic current flowing between the two compartments can be measured by a current detector.

In a specific embodiment, the current detector is a low-noise current amplifier connected to the nanopore. In certain embodiments, the current detector is sensitive for detecting changes in current on the order of 1-100, 10-100, 20-100, 20-50, 1-20 or 1-10picoamperes. In certain embodiments, the current detector can detect changes, in current, of at least 1, 10, 20, 30, 40, 50, 60, 70, 80, 90, or 100 picoamperes. It should have an input in a circuit where a known voltage can be supplied. Such detectors include, for example, voltage clamp amplifiers and transimpedance amplifiers.

In one embodiment, an external electric force can be applied via nanopore bias (Vpore) through the nanopore barrel, which can modulate the motion of biomolecules in the sample solution near the nanopipette tip. In some embodiments, the Vpore can be, for example, between +1V, ±900 mV, ±800 mV, f 700 mV, ±600 mV, ±500 mV, ±400 mV, ±300 mV, ±200 mV, ±100 mV, ±50 mV, ±20 mV, or ±10 mV.

In one embodiment, the first and second electrodes are not chemically modified. In one embodiment, the nanoelectrode surface is modified by recognition molecules, for example, antibodies, DNA oligomers, peptides, synthetic polymers, and small molecules with various functional groups, e.g., amine, amide, and/or carboxylic acid. In one embodiment, the surface of the nanopore, including outer and inner surface of the nanopore at the tip of the nanopipette, may be modified by silane molecules with various functional groups, e.g., 3-cyanopropyldimethlychlorosilane. The surface modification on the nanopore, nanoelectrode, and/or nanopipette may or may not immobilize or bind to the biomolecules in the sample solution.

In one embodiment, the nanopore has a conical shape. In one embodiment, the diameter of the nanopore is from about 5 nm to about 200 nm, from about 5 nm to about 150 nm, from about 5 nm to about 125 nm, from about 5 nm to about 100 nm, from about 10 nm to about 200 nm, from about 10 nm to about 150 nm, from about 10 nm to about 100 nm, from about 10 nm to about 90 nm, from about 10 nm to about 80 nm, from about 10 nm to about 70 nm, from about 10 nm to about 60 nm, from about 10 nm to about 50 nm, from about 10 nm to about 40 nm, from about 10 nm to about 30 nm, from about 10 nm to about nm, from about 20 nm to about 100 nm, from about 20 nm to about 90 nm, from about 20 nm to about 80 nm, from about 20 nm to about 70 nm, from about 20 nm to about 60 nm, from about 20 nm to about 50 nm, from about 20 nm to about 40 nm, or from about 20 nm to about 30 nm.

In one embodiment, the nanopore has a resistance ranging from about 0.1 to about 12 G$\Omega$, from about 0.2 to about 11 G$\Omega$, from about 0.5 to about 10 G$\Omega$2, from about 1 to about G$\Omega$, from about 1.5 to about 9.5 G$\Omega$, from about 1.5 to about 9 G$\Omega$, from about 2 to about 8.5 G$\Omega$, from about 2 to about 8 G$\Omega$, from about 2 to about 7.5 G$\Omega$, from about 2 to about 7 G$\Omega$, from about 2 to about 6.5 G$\Omega$, from about 2 to about 6 G$\Omega$, from about 2 to about 5.5 G$\Omega$, from about 2 to about 5 G$\Omega$, from about 2 to about 4.5 G$\Omega$, from about 2 to about 4 G$\Omega$, or from about 2 to about 3.5 G$\Omega$.

In one embodiment, the nanoelectrode extends out of the tip slightly having an effective area from about 0.01 to about 5 $\mu m^2$, from about 0.02 to about 4.5 $\mu m^2$, from about 0.05 to about 4 $\mu m^2$, from about 0.1 to about 3.5 $\mu m$ 2, from about 0.1 to about 3 $\mu m^2$, from about 0.1 to about 2.5 $\mu m$ 2, from about 0.1 to about 2 $\mu m^2$, from about 0.1 to about 1.5 $\mu m^2$, from about 0.1 to about 1 $\mu m^2$, from about 0.1 to about 0.5 $\mu m^2$, from about 0.01 to about 1 $\mu m^2$, from about 0.01 to about 0.5 $\mu m$ 2, from about 0.01 to about 0.2 $\mu m$ 2, from about 0.02 to about 1 $\mu m^2$, from about 0.02 to about 0.5 $\mu m$ 2, from about 0.02 to about 0.4 $\mu m$ 2, from about 0.02 to about 0.3 $\mu m^2$, or from about 0.02 to about 0.2 $\mu m$ 2.

In one embodiment, the effective diameter of the nanoelectrode ranges from about 5 nm to about 400 nm, from about 5 nm to about 300 nm, from about 5 nm to about 250 nm, from about 5 nm to about 200 nm, from about 10 nm to about 200 nm, from about 10 nm to about 150 nm, from about 10 nm to about 100 nm, from about 10 nm to about 90 nm, from about 10 nm to about 80 nm, from about 10 nm to about 70 nm, from about 10 nm to about nm, from about 10 nm to about 50 nm, from about 10 nm to about 40 nm, from about 10 nm to about 30 nm, from about 10 nm to about 20 nm, from about 20 nm to about 100 nm, from about 20 nm to about 90 nm, from about 20 nm to about 80 nm, from about 20 nm to about 70 nm, from about 20 nm to about 60 nm, or from about 20 nm to about 50 nm.

In a specific embodiment, the surface of the nanopipette is negatively charged.

In one embodiment, the system, apparatus and/or device is applied to study the intermolecular interactions between small biomolecules in a crowded environment. The dramatic concentration changes of enriched biomolecules at the tip also induces changes in the ionic current signals and leads to high SNR.

In one embodiment, the system, apparatus and/or device further comprises a potential detector and/or a current detector.

In one embodiment, the translocation events of biomolecules through the nanopore are very sensitive to the size ratio between biomolecule and the nanopore. For example, the ratio of biomolecule to nanopore, e.g., in size, or dimension, may be at least 1:1.1, 1:1.2, 1:1.3, 1:1.4. 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:16, 1:17, 1:18, 1:19, 1:20 or any ratio therebetween.

In certain embodiments, the subject invention provides methods of detecting, diagnosing, monitoring and/or managing conditions in a subject. Detection of a biomarker/biomolecule in a sample can be indicative, or confirmatory, of a diagnosis of a condition. Monitoring can include detection or repeated detection of a biomarker/biomolecule from a sample or samples of a subject in which the biomarker/biomolecule has already been detected. Managing can include therapeutic intervention based upon the presence or absence of a biomarker/biomolecule in a subject. On the basis of the detection of the presence, absence or quantity of a biomarker/biomolecule in a subject, a treatment can be selected, administered, monitored, and/or modified. Detection of the presence, absence or quantity of a biomarker/biomolecule in a subject can comprise detection of a biomarker/biomolecule in a sample from the subject.

The detection methods described herein can be performed on a subject or on a sample from a subject. A sample can contain, or be suspected of containing, a biomarker/biomolecule. A sample can be a biological sample from a subject. The subject can be a subject having, diagnosed with, suspected of having, at risk for developing a condition, or even a subject without any indicia of the condition. In certain embodiments, the sample can be a blood sample, a serum sample, a plasma sample, a cerebrospinal fluid sample, or a solid tissue sample. A sample solution is formed with a sample from a subject. In certain embodiments, the sample may be cell culture medium, cell extract or cell lysate.

The subject can be an animal subject, preferably a mammal and most preferably a human. The subject may be, but is not limited to, non-human primates, rodents (e.g., rats, mice), dogs, cats, horses, cattle, pigs, sheep, goats, chickens, guinea pigs, hamsters and the like.

Advantageously, low molecular weight proteins less than 10 kDa can be detected using the provided system and method. The motion of the biomolecule in solution can be driven by thermal fluctuations or external electric field. Because of the high mobility of small biomolecules, no external bias (Vpore) is normally needed to achieve high throughput detection.

In one embodiment, the subject invention provides a method for detecting a biomolecule in a sample by using the system, apparatus and/or device of the subject invention. The method of using the system, apparatus and/or device comprises introducing a sample solution containing the biomolecule into the nanopipette, or the open barrel of the nanopipette, dipping the tip of the nanopipette in a crowding agent (e.g., hydrogel), wherein the nanopore at the tip of the nanopipette connects the crowding agent (e.g., hydrogel) to the sample solution containing the biomolecule, enabling the biomolecules in the sample solution to flow through the nanopore, and measuring a signal or signal change upon translocation of the biomolecule. As the biomolecules flow through the nanopore, a current signal can be recorded and analyzed to provide various measured parameters of the biomolecules, including size, shape, charge, concentration and so on.

In one embodiment, the method for a label-free detection, quantification and/or characterization of a biomolecule in a sample, comprises contacting the sample with the system, apparatus and/or device of the subject invention, which comprises a nanopipette, and measuring a signal, e.g., a transient current change due to the translocation of the biomolecule through the nanopore of the nanopipette.

In specific embodiments, the nanoelectrode is a CNE made from a single-barrel nanopipette or double-barrel nanopipette, or electrochemically etched tip from metal wires or other nanofabrication methods known in the art. In a specific embodiment, the metal wire is, for example, copper, titanium, palladium, silver, platinum, or gold.

In one embodiment, the method for detecting, quantifying and/or characterizing a biomolecule, preferably, at a single molecule level, comprises providing a sample containing a biomolecule or suspected to contain the biomolecule; contacting the sample with the system, apparatus and/or device of the subject invention; and measuring and/or monitoring the current change for detecting, quantifying or characterizing the biomolecule.

In one embodiment, the method for detecting, quantifying and/or characterizing a biomolecule, preferably, at a single-entity level, comprises providing a sample containing a biomolecule or suspected to contain the biomolecule; adding the sample to the nanopipette or the open barrel of the nanopipette of the device or system of the subject invention; and detecting, quantifying or characterizing the biomolecule by measuring and/or monitoring the current change.

In one embodiment, the step of detecting, quantifying or characterizing the biomolecule comprises measuring a current flow over time as individual biomolecules pass through the nanopore, measuring a potential change of the nanoelectrode over time, and/or measuring a resistance.

In one embodiment, the step of detecting, quantifying or characterizing the biomolecule may further comprise determining the translocation events of the biomolecule in the sample or solution, and/or through the nanopore from current measurements.

In one embodiment, the method of the subject invention may further comprise a step of applying a potential via nanopore bias through the nanopore barrel prior to any measurements.

In one embodiment, the method of the subject invention further comprises analyzing the measured current, potential and/or resistance to obtain the various parameters of the biomolecule, including size, shape, and charge.

In one embodiment, the step of detecting, quantifying and/or characterizing the biomolecule may further comprise comparing the obtained parameters to a standard, e.g., known parameters and signatures of the biomolecule.

The biomolecules can be, for example, compounds, drugs, proteins, peptides, enzymes, antibodies, nucleotides, DNAs, and RNAs. In some embodiments, the biomolecules are proteins having a molecular weight of at least 500 Da, at least 750 Da, at least 1 kDa, at least 5 kDa, at least 10 kDa, at least 15 kDa, at least 20 kDa, at least 25 kDa, at least 30 kDa, at least 35 kDa, at least 40 kDa, at least 45 kDa, at least 50 kDa, at least 55 kDa, at least 60 kDa, at least 65 kDa, at least 70 kDa, at least 75 kDa, at least 80 kDa, at least 85 kDa, at least 90 kDa, at least 95 kDa, at least 100 kDa, at least 125 kDa, at least 150 kDa, at least 200 kDa, at least 250 kDa, at least 300 kDa, at least 350 kDa, at least 400 kDa, at least 450 kDa, at least 500 kDa or any molecular weight in between.

In certain embodiments, the biomolecules are positively or negatively charged proteins having a molecular weight of less than 100 kDa, less than 90 kDa, less than 80 kDa, less than 70 kDa, less than 60 kDa, less than 50 kDa, less than 40 kDa, less than 30 kDa, less than 20 kDa, less than 10 kDa, less than 5 kDa, or less than 1 kDa.

In specific embodiments, the biomolecules are small molecules having a size of less than 50 nm, less than 45 nm, less than 40 nm, less than 35 nm, less than 30 nm, less than 25 nm, less than, 20 nm, less than 15 nm, less than 10 nm, less than 5 nm, less than 2 nm, less than 1 nm, or any size therebetween.

In specific embodiments, the biomolecules that can be detected include, but are not limited to, ATP, ADP, AMP, GTP, GDP, GMP, cytochrome-c (12 kDa), insulin (5.8 kDa), HMGA2, hemoglobin, IgG, bovine serum albumin (BSA), ferritin and lysozyme.

In one embodiment, the subject invention also provides a method for detecting, quantifying and/or characterizing a biomolecule in a sample solution, preferably, at a single-entity level, the method comprising:
  providing a nanopipette sensor comprising a nanopipette, and a reference electrode, wherein the nanopipette comprises a nanopore barrel, disposed with a working electrode and back-filled with a solution comprising the biomolecule;
  immersing the nanopipette in a crowding agent (e.g., hydrogel), and placing the reference electrode in the crowding agent (e.g., hydrogel);
  optionally, applying a potential between the working electrode and the reference electrode, and
  detecting, quantifying and/or characterizing the biomolecule in the sample solution by measuring and/or monitoring the current flow through the nanopore.

In one embodiment, the crowding agent is a hydrogel or polymer. In a preferred embodiment, the hydrogel is an ion and small molecule permeable hydrogel. In a specific embodiment, the hydrogel is fibrin.

A variety of electrolyte solutions may be used in the nanopipette. The electrolyte solutions contain dissolved electrolytes, i.e., free ions. Typical ions include sodium, potassium, calcium, magnesium, chloride, phosphate and bicarbonate. Other ionic species may be used. The electrolyte should carry an ionic current. The electrolyte solution may comprise from about 5 to about 160 mM, from about 10 to about 150 mM, from about 10 to about 140 mM, from about 10 to about 130 mM, from about 10 to about 120 mM, from about 10 to about 110 mM, from about 10 to about 100 mM, from about 10 to about 90 mM, from about 10 to about 80 mM, from about 10 to about 70 mM, from about 10 to about 60 mM, from about 10 to about 50 mM, from about 10 to about 40 mM, from about 10 to about 30 mM, or from about 10 to about 20 mM, of positive and negative ionic species.

A variety of salts may be used in the electrolyte solution. They are composed of cations (positively charged ions) and anions (negative ions) so that the product is electrically neutral (without a net charge). These component ions can be inorganic such as chloride (Cl—), as well as organic such as acetate ($CH_3COO^-$) and monatomic ions such as fluoride (F—), as well as polyatomic ions such as sulfate ($SO_4^{2-}$). There are several varieties of salts. Salts that hydrolyze to produce hydroxide ions when dissolved in water are basic salts and salts that hydrolyze to produce hydronium ions in water are acid salts. Neutral salts are those that are neither acid nor basic salts. Molten salts and solutions containing dissolved salts (e.g., sodium chloride in water) are called electrolytes, as they are able to conduct electricity.

In one embodiment, the same or different electrolyte solution may be used in the nanopipette and the hydrogel solution. In one embodiment, the electrolyte solution is saline, such as PBS. In one embodiment, the electrolyte solution has a physiological solution comprising a salt or salts that are essentially isotonic with body fluid.

In certain embodiments, the sample solution may have a pH value from 3 to 11, 3 to 10, 4 to 10, 5 to 9, or 6 to 8 or other range between 3 and 11. In one embodiment, the sample solution has a physiological pH.

In one embodiment, the subject invention provides a method for detecting intermolecular interactions between small biomolecules. The intermolecular interaction between biomolecules is very important and complex. Proteins interact with each other and act as molecular machines. The interactions are present in all living beings in terms of different biological processes such as DNA replication, DNA transcriptions, and catalytic metabolism.

The method of the subject invention can also be used to investigate the interaction mechanism of biomolecules. The conically shaped nanopipette tip with long taper provides an ideal reaction space with strong nanoconfinement. When hydrogel is present outside the nanoscale orifice, they further suppress the translocation speed of biomolecules. More molecules are accumulated at the tip. When a bias is applied from the backend of nanopipette, the molecules are pressed into the confined space of the nanopipette tip. Due to the crowded space and the external electric force, the molecules can interact by overcoming the electrostatic repulsion and steric hindrance. For example, the dimmer formation of peptides, the protein-protein interaction, the hydrogen bonding interactions between DNA nucleotides and the formation of G-quadruplex (G4) of GTP can be observed.

In certain embodiments, the method for detecting intermolecular interactions between small biomolecules comprises introducing a sample solution containing the biomolecules into the nanopipette, or the open barrel of the nanopipette, dipping the tip of the nanopipette in a crowding agent (e.g., hydrogel), wherein the nanopore at the tip of the nanopipette connects the crowding agent (e.g., hydrogel) to the sample solution containing the biomolecules, enabling the biomolecules in the sample solution to crowd at the tip of the nanopipette, and measuring a signal or signal change upon translocation of the biomolecule.

In some embodiments, the method for detecting intermolecular interactions between small biomolecules comprises providing a sample containing two or more biomolecules or suspected to contain the two or more biomolecules; contacting the sample with the system, apparatus and/or device of the subject invention; and measuring and/or monitoring a current change, wherein the two or more biomolecules can be the same or different biomolecules.

In certain embodiments, the method for detecting intermolecular interactions between small biomolecules comprises providing a sample containing two or more biomolecules or suspected to contain the two or more biomolecules; adding the sample to the nanopipette or the open barrel of the nanopipette of the device or system of the subject invention; and measuring and/or monitoring a current change, wherein the two or more biomolecules can be the same or different biomolecules.

In one embodiment, the subject invention also provides a method for detecting intermolecular interactions between small biomolecules, the method comprising:
  providing a nanopipette sensor comprising a nanopipette, and a reference electrode, wherein the nanopipette comprises a nanopore barrel, disposed with a working electrode and back-filled with a solution comprising the biomolecules;
  immersing the nanopipette in a crowding agent (e.g., hydrogel), and placing the reference electrode in the crowding agent (e.g., hydrogel);
  optionally, applying a potential between the working electrode and the reference electrode, and measuring and/or monitoring the current flow through the nanopore.

In some embodiments, the method for detecting intermolecular interactions between small biomolecules may further comprises comparing the signal recorded to a control signal.

In one embodiment, the subject invention provides a method for accumulating small biomolecules at the tip of a nanopipette, the method comprises introducing a sample solution containing the biomolecules into the nanopipette, or the open barrel of the nanopipette, and dipping the tip of the nanopipette in a crowding agent (e.g., hydrogel), wherein the nanopore at the tip of the nanopipette connects the crowding agent (e.g., hydrogel) to the sample solution containing the biomolecules, enabling the biomolecules in the sample solution to crowd at the tip of the nanopipette.

In some embodiments, the method for accumulating small biomolecules at the tip of a nanopipette comprises providing a sample containing biomolecules or suspected to contain the biomolecules; contacting the sample with the system, apparatus and/or device of the subject invention; and measuring and/or monitoring a current change.

In certain embodiments, the method for accumulating small biomolecules at the tip of a nanopipette comprises providing a sample containing biomolecules or suspected to contain the biomolecules; adding the sample to the nanopipette or the open barrel of the nanopipette of the device or system of the subject invention; and measuring and/or monitoring a current change.

In one embodiment, the subject invention also provides a method for accumulating small biomolecules at the tip of a nanopipette, the method comprising:
  providing a nanopipette sensor comprising a nanopipette, and a reference electrode, wherein the nanopipette comprises a nanopore barrel, disposed with a working electrode and back-filled with a solution comprising the biomolecules;

immersing the nanopipette in a crowding agent (e.g., hydrogel), and placing the reference electrode in the crowding agent (e.g., hydrogel);

optionally, applying a potential between the working electrode and the reference electrode, and measuring and/or monitoring the current flow through the nanopore.

In one embodiment, the subject invention provides a method for slowing down the translocation of small biomolecules through the nanopore of a nanopipette, the method comprises introducing a sample solution containing the biomolecules into the nanopipette, or the open barrel of the nanopipette, dipping the tip of the nanopipette in a crowding agent (e.g., hydrogel), wherein the nanopore at the tip of the nanopipette connects the crowding agent (e.g., hydrogel) to the sample solution containing the biomolecules, enabling the biomolecules in the sample solution to crowd at the tip of the nanopipette, and measuring a signal or signal change upon translocation of the biomolecule.

In some embodiments, the method for slowing down the translocation of small biomolecules through the nanopore of a nanopipette comprises providing a sample containing biomolecules or suspected to contain the biomolecules; contacting the sample with the system, apparatus and/or device of the subject invention; and measuring and/or monitoring a current change.

In certain embodiments, the method for slowing down the translocation of small biomolecules through the nanopore of a nanopipette comprises providing a sample containing biomolecules or suspected to contain the biomolecules; adding the sample to the nanopipette or the open barrel of the nanopipette of the device or system of the subject invention; and measuring and/or monitoring a current change.

In one embodiment, the subject invention also provides a method for slowing down the translocation of small biomolecules through the nanopore of a nanopipette, the method comprising:

providing a nanopipette sensor comprising a nanopipette, and a reference electrode, wherein the nanopipette comprises a nanopore barrel, disposed with a working electrode and back-filled with a solution comprising the biomolecules;

immersing the nanopipette in a crowding agent (e.g., hydrogel), and placing the reference electrode in the crowding agent (e.g., hydrogel);

optionally, applying a potential between the working electrode and the reference electrode, and measuring and/or monitoring the current flow through the nanopore.

In one embodiment, the method and system of the subject invention can be used to determine the charge and motion of a biomolecule, e.g., protein, from non-specific molecule-substrate surface interaction events. Such determination comprises analyzing the shape and magnitude of a recorded time-resolved potential change and its time derivative. In some embodiments, the charge variation of the biomolecule, e.g., protein, at different pH can also be determined.

In one embodiment, the method of the subject invention can be used to detect the net charge variation of a single biomolecule, e.g., protein induced by a pH change. Combined with molecular dynamic (MD) and finite element method (FEM) simulations, this variation likely originates from the intrinsic flexibility and nonuniformly distributed surface charge of the protein.

In one embodiment, the method can be used for protein binding and binding dynamic analysis, such as a binding event of the biomarker molecule to an antibody. Similar techniques for ensemble measurements are ELISA (enzyme-linked immunosorbent assay) and SPR (surface plasmon resonance).

In certain embodiments, the crowding agent is selected from, for example, various types of hydrogel, high molecular weight polymers like PEG 20 k, and combinations thereof.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists of" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting of" or "consists essentially of" indicate that the claim encompasses embodiments containing the specified materials or steps and those that do not materially affect the basic and novel characteristic(s) of the claim. Use of the term "comprising" contemplates other embodiments that "consist of" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Methods

Reagent and Material.

Equine spleen ferritin (ferritin), horse heart cytochrome c (cyt c), insulin, and lysozyme from chicken egg white (lyz), polyethylene glycol (PEG) 8000 (89510), microperoxidase (MP-11), Adenosine Triphosphate (ATP), Guanosine Triphosphate (GTP), Deoxythymidine triphosphate (dTTP), and FITC dye used in the experiments were purchased from the MilliporeSigma. Molecules in the powder form are dissolved in 1×PBS solution with desired concentration to prepare the stock solutions. The concentration of stock solution for some biomolecules was further checked by using UV-Vis spectrometer. The molecule solutions used in experiments were prepared by diluting the stock solution using 1×PBS with the typical concentration in the range from 100 to 500 pM. The 1×PBS solution (pH 7.4) was prepared by dissolving PBS powder (8.0 g of NaCl, 2.89 g of $NaHPO_4 \cdot 2H_2O$, 0.2 g of KCl, g of $KH_2PO_4$) in 1000 ml of deionized (DI) water. All solutions were prepared using DI water (~18 MΩ) (LabChem, ACS Reagent Grade, ASTM Type I).

Fabrication and Characterization of Multifunctional Nanopipette.

The multifunctional nanopipettes were fabricated from quartz theta capillary tubes (FG-QT120-90-7.5, shutter instrument). In brief, the quartz theta pipettes were first cleaned by piranha solution (mixture of con. Sulfuric acid and hydrogen peroxide in the ratio 3:1,) and then pulled by a laser puller (P-2000, shutter Instrument) with the following parameters: Heat=825, FIL=3, VEL=220, PUL=190. Then one of the barrels was filled with pyrolytic carbon to form the carbon nanoelectrode (CNE). The nanopore size was estimated based on the measured ionic conductance from the current-voltage (i-v) plots. Depending on the size of biomolecules, the diameters of the prepared nanopipette nanopores are in the range from 15-70 nm. The effective surface area of CNE was estimated from the cyclic voltammogram (CV), which is in the range from 0.15-0.9 $\mu m^2$ with an average effective surface area of ~0.3

Experimental Setup for Single Molecule Detection.

Figure 2A:
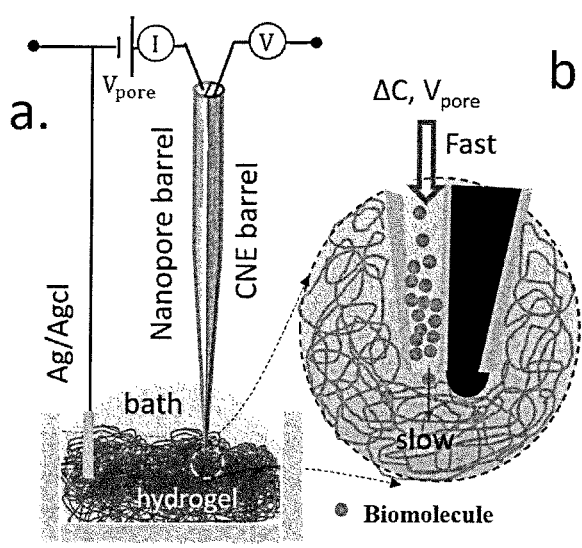
FIGS. 2A-2B. (2A) A schematic illustration of the experimental setup. The zoomed in illustrates the accumulation of molecules at the tip. (2B) (i) The optical microscope image for the side view of a typical nanopipette tip. The dark side is the CNE barrel filled with pyrolytic carbon. (ii) The optical microscope image of the nanopipette tip before loading the fluorescence dye FITC. (iii-iv) Fluorescence images of the nanopipette at zero bias immediately (iii) and 20 min (iv) after loading the 40 μM FITC dye. (v) AFM topography image in tapping mode of the dried fibrin hydrogel on the mica surface.

The ionic current-time (i-t) and potential-time (v-t) were recorded using an experimental setup as shown in FIG. 2A. The electrochemical measurement was performed using Axopatch 200B amplifier (Molecular Devices Inc., CA). Freshly prepared Ag/AgCl wires were used as electrodes and a battery-powered high impedance differential amplifier was used to measure the open-circuit potential of the CNE. The bandwidth of low pass filter is 5 kHz for current and 40 kHz for potential signals. The data were recorded by a Yokogawa oscilloscope (DL850) with a sampling rate of 50 kHz. All experiments and measurements were performed at room temperature.

Fibrin Hydrogel Fabrication and Characterization.

Sterile Fibrinogen from human plasma (MilliporeSigma, F3879) was first dissolved in 1×PBS at 35 mg/ml and kept at 37° C. for about two hours. Thrombin from human plasma (MilliporeSigma, 9002044) was dissolved in 1x PBS at 100 U/ml. Thrombin solution was then added to the Fibrinogen solution with a 1:3 ratio by volume at 37° C. The mixture of about 100 µl was left in a small PDMS chamber for about 20 mins to form hydrogel. We then added about 20 µL of 1×PBS solution to the surface of the hydrogel. The topography images of fibrin hydrogel were collected by atomic force microscopy (AFM) (XE-Bio system, Park system Inc Santa, CA) in contact mode (CM) with cantilevers whose stiffness was 0.4 N/m. To prepare the sample for AFM imaging, few drops of freshly prepared fibrin hydrogel (~30 µl) are dried on the freshly cleaved mica surface for 10-20 min. The acquired images are processed using Image J.

Data Reproducibility and Analysis.

To guarantee the reproducibility of the results, the measurements for each biomolecule have been repeated by at least three nanopipettes. The ionic current and potential data were analyzed by using custom programs written in Labview and the figures were processed by Originpro 2018b. Moving average smoothing method with a 2 ms time window is typically applied to the data before statistical analysis.

Example 1—Maximize Nanoconfinement and Induce Molecule Crowding

Figure 2B:
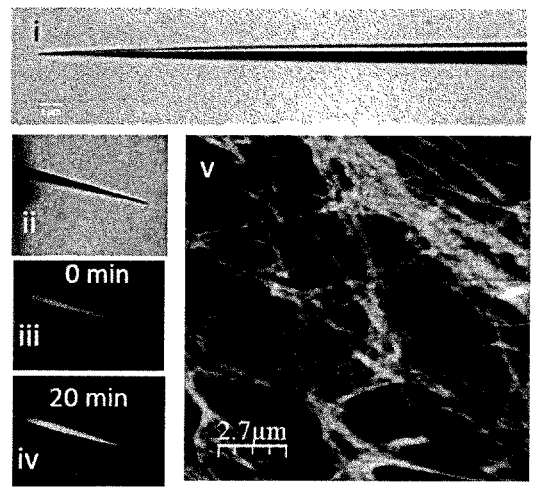

As shown in FIG. 2B(i), long taper quartz nanopipettes were used to enhance the nanoconfinement effect. The biomolecules are loaded from the backend of the nanopore barrel and allowed to pass through the long nanochannel before they exit from the nanopore, FIG. 1b(ii). Nanopipette with the nanopore diameter about 5-15 times bigger than the size of molecules were typically used. The bigger size ratio between the nanopore and the biomolecule can reduce the electrostatic repulsion between the negative surface charge of quartz surface and negatively charged biomolecules, and the chances of clogging at the nanopipette tip for positive biomolecules.

Small biomolecules with a size of a few nanometers could reach the tip just by diffusion within a time from a few minutes to tens of minutes depending the chemical and physical properties of the biomolecule (such as, size, shape, charge) and the pore molecule size ratio. To demonstrate this, the fluorescence images of the nanopipette tip loaded with 40 µM FITC dye solution are shown in FIG. 2B at 0 min (iii) and 20 min (iv). The intensity increase at the tip suggests more FITC molecules diffuse and concentrate at the nanopipette tip in 20 min without applying any nanopore bias ($V_{pore}$).

For larger charged biomolecules such as ferritin with about 12 nanometer size, their mass transport toward the tip can be assisted by electrophoresis via the applied $V_{pore}$. It should be noted that the CNE is not necessary here for the nanoconfinement and molecule enrichment. The CNE was used to probe the changes of local electrostatic environment, including the crowding at the tip.

However, nearly 10 times size ratio between the nanopore and biomolecule make the nanoconfinement effect at the nanopipette tip still not effective to enrich small biomolecules. A crowding agent was therefore introduced outside the tip to further hinder the exit of biomolecules from the nanopipette nanopore. The often-used macromolecule crowding agent PEG-8 k was added in the outer bath solution to hinder the translocation speed of the biomolecules. However, the PEG-8 k is not dense enough to hinder the motion of small biomolecules and induce self-crowding and thus the small biomolecules and their interactions cannot be detected. Thus, fibrin hydrogel was selected as next approach.

The semi-permeable fiber of fibrin hydrogel can be used to detect and probe the interaction of smaller molecules like short peptides and DNA bases in a nanopipette based single molecule sensing platform. The AFM image in FIG. 2B (v) shows that the fibrin hydrogel is a dense mesh formed by large number of fibrin fibers with micron and nanometer diameters. The addition of fibrin hydrogel is highly effective such that even small biomolecules with size about 1 nm can be concentrated and confined in the tip.

Example 2—Nanoconfinement and Self-Crowding Enhanced Single Molecule Detection The approach can be used to detect a variety of biomolecules. FIG. 3 shows the representative results of cyt c using the nanopipette with a nanopore size of ~22 nm and CNE effective surface area of ~0.9 μm². The positively charged cyt c at the neutral pH has a molecular weight of ~12.5 kDa with its hydrodynamic diameter of ~3.5 nm was used as model single molecule.

As shown in FIGS. 3A and 3B, before adding cyt c in the nanopore barrel, both the i-t (black) and v-t (gray) traces are stable and featureless when placing the tip in the 1×PBS solution or in the hydrogel. However, the baseline acquired in the hydrogel was more stable with smaller noise than that in the 1×PBS.

To avoid the complication due to $V_{pore}$, the data with zero $V_{pore}$ were only shown here. After loading 500 pM cyt c in the nanopipette barrel from the backend, followed by waiting for about 1 hour in the room temperature to let the cyt c diffuse to the tip, measurements were carried out. After placing the cyt c loaded nanopipette tip in the bath solution (1x PBS) above the hydrogel and waiting for a few minutes, individual transient current spikes with low event rate (~1 s$^{-1}$) were observed (FIG. 3B). The upward current spikes appearing in the i-t trace are due to the translocation events of cyt c. The events were recorded for about 20 min and the spikes appeared with a relatively constant event rate. No obvious accumulation of cyt c was observed.

The cyt c loaded nanopipette tip was further lowered and inserted into the fibrin hydrogel. The insertion was indicated by a slight decrease in current baseline even at the zero $V_{pore}$. The recording was started from 0 mV bias. Generally, in most of the experiments, the molecules were loaded ~1-2 hr before the electrical measurements. Typically, for the fair comparison of time evolution of event rate in PBS and in fibrin hydrogel, the same ~1 hr waiting period was carried out before conducting the measurement.

During the electrical measurement, the waiting period is larger in fibrin hydrogel than in PBS to observe the translocation signal. The longer waiting time in fibrin hydrogel is attributed to the hindered diffusion. When the translocation signal started, a slight decrease was observed in current baseline (slightly more negative), which is attributed to the accumulation of cyt c proteins near the vicinity of the orifice.

As shown in FIG. 3C, the density of the current spikes is high in the i-t trace. The event rate is about ~20 s$^{-1}$, which is almost 20 times higher than the event rate observed in 1×PBS solution. Meanwhile, simultaneous changes were also observed in the v-t trace (gray), suggesting the improved potential sensitivity of the CNE. The gradual decrease (less negative) of the potential baseline was also observed, which is also attributed to the accumulation of positively charged cyt c proteins near the vicinity of the orifice.

Different from the relatively stable event rate detected in 1×PBS solution, the current spike event rate is highly dynamic in the hydrogel. As shown in FIG. 3D, the event rate increases significantly in the first 4 min then remains at the high level for the following 6-8 min. After about 15 min, the event rate gradually falls to ~1-2 s$^{-1}$. The dynamic changes of current spike event rate reflect the accumulation and the depletion of the proteins at the tip.

The scatter plots of the current spike amplitude (ΔI) vs. spike duration ($t_d$) are shown in FIG. 3E. The data clearly displays two different set of data. The mean $t_d$ of the current spike for cyt c in PBS and hydrogel at the zero bias was 3.1±0.5 ms and 6.5±0.5 ms, respectively. The histograms of $t_d$ from both the PBS (black) and fibrin hydrogel (dark gray) cases are shown in FIG. 3F. The mean $t_d$ for the fibrin case has increased by more than two times. Therefore, the translocation speed of cyt c is slowed due to the fibrin hydrogel outside the orifice. The histograms of signal-to-noise ratio (SNR) of the current spikes for both cases were also compared. The SNR of a current spike was defined as the ratio between ΔI and the RMS value of baseline current Irms. The mean SNR of current spikes detected in hydrogel increased almost two times. Therefore, the crowding of cyt c also helps to reduce the ionic current noise.

The accumulation of proteins can be effectively controlled by the applied $V_{pore}$. After the depletion of the previous batch of accumulated proteins, the event rate gradually decreased and became very low (~1-2 s$^{-1}$) at 0 mV bias. A higher positive $V_{pore}$ (+300 mV) was then applied to drive more proteins to the tip by electrophoresis and cyt c proteins again were accumulated at the tip. After applying +300 mV for 20 sec, the current baseline reduced about 20% of the initial value.

The left side in FIG. 3G shows a segment of an ionic current trace during the first half of i-t trace. The current baseline continues to decrease, suggesting the gradual accumulation of cyt c near the nanopipette orifice. Then clusters of densely packed spikes started to appear, which are due to the accumulated cyt c near the tip (see the middle trace of FIG. 3G). After the appearance of many spikes in the cluster form, the appearance of spikes became sparse and the current baseline again returned to the initial level (see the third trace at the right side of FIG. 3G), suggesting this batch of accumulated cyt c proteins again dissipated away from the tip.

Interestingly, the shape and directionality of the current spikes in an accumulated cluster changed significantly (see FIG. 3H). As demonstrated in the middle trace of FIG. 3G, the downward resistive spikes (as indicated by transient decrease in ionic current) appeared at the beginning (time interval ~41 ms) and end (time interval ~68 ms) of a cluster. The upward conductive spikes (as indicated by transient increase in current amplitude) appeared in the middle of the cluster with the mean interval of ~14 ms. The similar trend was also observed for the change of current spike duration ($t_d$) over a cluster. The middle conductive spikes were faster (~6 ms) than the spikes at the beginning (~10 ms) and end (~12 ms) of the cluster. In contrast, the event rate of conductive spikes in the middle of the trace was more than 3 times higher (~66 s$^{-1}$) than at the beginning (—19 s$^{-1}$) and the end (23 s$^{-1}$) of the cluster. This phenomenon can be explained by the dynamic change of the local cyt c concentration in each concentrated cluster. The concentration of cyt c is higher in the middle that deplete the ion concentration and the lower at both ends of cluster, which is also supported by the observed changes of event rate and time interval between neighboring spikes. The concentration variation of cyt c in the confined space at the tip effectively module the local ion concentration by volume exclusion and charge neutrality, leading to a highly non-uniform ion concentration distribution across the cyt c cluster. The current spikes can change from resistive to biphasic and to conductive spikes with the decrease of local ion concentration. Therefore, the shape change of the current spike here also reveals the interesting phenomenon of local ion concentration and the crowding condition.

Example 3—Effective Regulation of Small Biomolecule Enrichment at Nanopipette Apex by bias To investigate the effect of crowding on small biomolecule detection, heme peptide MP-11 was chosen as a model. In the further experiment, this method was applied to detect even small biomolecules such as a DNA base. The working mechanism of this method is to generate crowding of biomolecules that can effectively reduce the actual nanopore size to the size of molecule level.

FIG. 4 shows the representative data of negatively charged MP-11, which has only 11 amino acids with its molecular weight of about 1.9 kDa. The solution containing 100 pM MP-11 was backfilled in a nanopipette with the nanopore size of ~16 nm and the CNE effective diameter of ~0.45 μm.

Before the measurement, a waiting period of 1-2 hr was applied to let the MP-11 molecules diffuse to the tip. At the beginning of the measurement with zero $V_{pore}$, a few small upward current spikes were observed stochastically due to the resistive events of MP-11. Typically, after 5-10 min, dense current spikes appeared in a cluster form (see FIG. 4A), suggesting that the accumulated MP-11 molecules appear in the cluster form at the tip. For the small molecules like MP-11, the appearance of crowded clusters was observed earlier than the bigger proteins such as cyt c, which was attributed to the higher mobility of the smaller molecule.

In addition, the dependence of $V_{pore}$ on the formation of crowded MP-11 clusters was also studied. The $V_{pore}$ magnitude with 10 s of mV is already enough to drive them to the tip. The i-t traces in FIG. 4A reveals the cluster formation at different $V_{pore}$. The size and density of the formed MP-11 clusters were defined based on the number of spikes and event rate. The applied $V_{pore}$ can effectively regulate the size and the degree of crowding of each cluster.

Figures 4A, 4B:
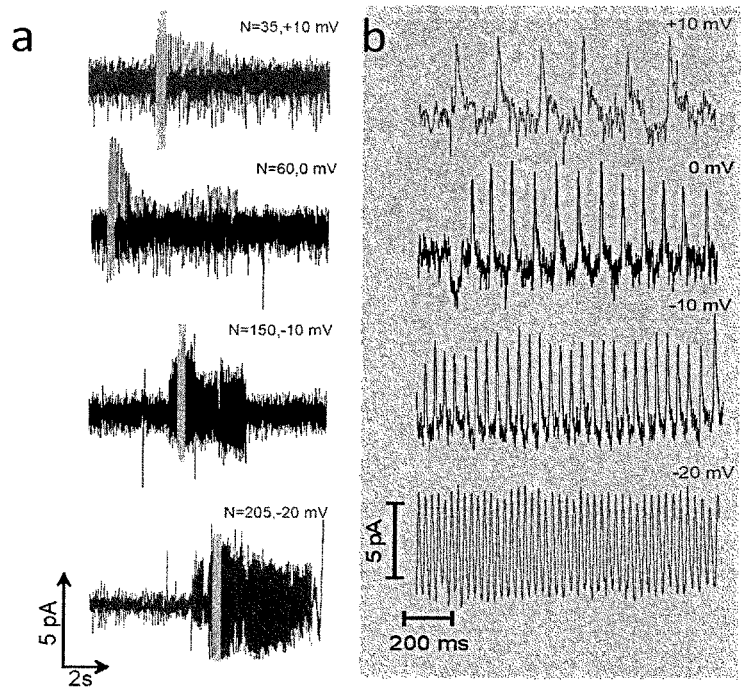
FIGS. 4A-4E. The bias dependence enrichment of MP-11. (4A) The i-t traces show the cluster formation of MP-11 at different $V_{pore}$: +10 mV, 0 mV, −10 mV, and −20 mV in the presence of fibrin hydrogel. The concentration of loaded MP-11 solution is 100 pM. (4B) The zoomed-in traces inside each cluster of traces in (4A). (4C) The plot of event rate vs. $V_{pore}$. The line is the eye guide. (4D) The distribution of dwell time as a function of $V_{pore}$ was plotted as merged histogram. (4E) single merged scatterplot of the bias dependence MP-11 translocation data.

As shown in FIG. 4A, the cluster size increased with the increase of the magnitude of the negative $V_{pore}$. Inside each formed cluster, the event rate (cluster density) is obviously higher at the more negative $V_{pore}$ (see FIG. 4B), along with the reduced time interval between two neighboring spikes. It was also interesting to note that current spikes and the cluster formation can still be observed at the small opposite bias (+10 mV) though the cluster size is smaller. However, the speed of the molecule is very slow at the small positive bias.

Figure 4C:
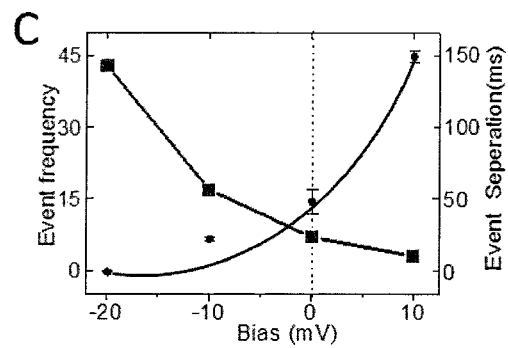

The number of events over a cluster was used for the statistical analysis. The mean event rate inside the accumulated cluster as a function of $V_{pore}$ is shown in FIG. 4C. The initial event rate at 0 mV bias was nearly 3 s$^{-1}$ When the bias was increased to −10 mV, the event rate increased 2.5 times to 7 s$^{-1}$ However, the event rate decreased almost 2 times when the $V_{pore}$ was changed to +10 mV. The distribution of dwell time as a function of $V_{pore}$ was plotted as merged histograms as in FIG. 4D. The dwell time decreases and becomes more uniform when the $V_{pore}$ is more negative. The positive bias slows down the speed of MP-11 moving towards the nanopore, as shown in the increased dwell time (mean value 26±8 ms).

Figures 4D, 4E:
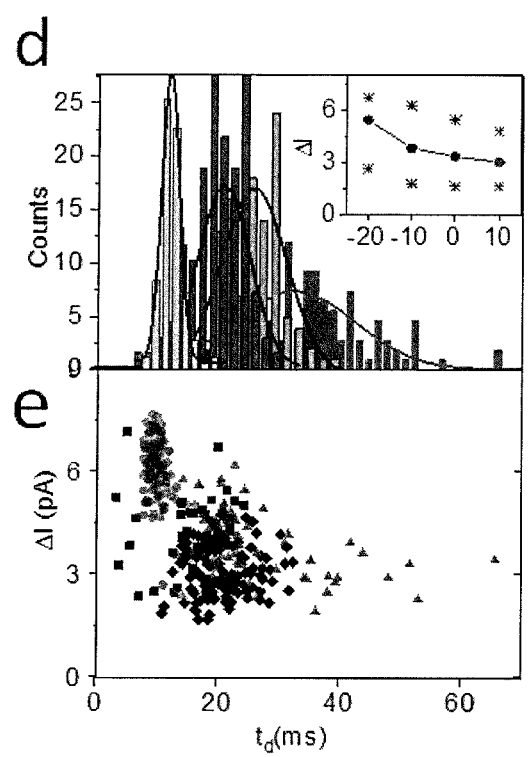

Increased crowding of molecules also has a noticeable effect on current spike amplitude ΔI. FIG. 4E represents single merged scatterplot of the bias dependence of ΔI. The data points in dark gray illustrates the events recorded at +10 mV, black at 0 mV, gray at −10 mV and light gray at −20 mV bias. The mean value of ΔI is obviously higher with a smaller distribution at −20 mV because of the increased crowding.

Example 4—Enhancing the Detection of Small Biomolecules by Adding Crowding Macromolecules in the Cis Side With the enhanced confinement from both the long nanochannel at the cis side and the hydrogel at the trans side of the nanopipette nanopore, small biomolecules driven by concentration gradient or/and the applied $V_{pore}$ effectively accumulate. To further gain insight into crowding-enhanced sensitivity of small biomolecule detection, on adding larger non-reacting biomolecules as the crowding agent at the cis side, the sensitivity of smaller biomolecules can be better improved. In this way, the size requirement of the nanopore can be further relaxed while detecting the small biomolecules.

In one example, to create a crowded environment at the cis side in the nanopipette tip, ferritin proteins with ~480 kDa molecular weight and ~12 nm hydrodynamic diameter, were used as the crowding agent for the detection of hormone insulin, a small protein with 51 amino acids and ~5.5 kDa molecular weight. The insulin is likely to exist as the dimer form in the experiments.

Before the measurement, 500 pM ferritin solution in 1×PBS was first added in the nanopipette with the nanopore diameter ~40 nm and the effective nanoelectrode diameter ~0.33 inn and waited at room temperature for ~2 hr. The nanopore size is about 20 times bigger than the size of insulin. Since, both ferritin and insulin are negatively charged at neutral pH, negative $V_{pore}$ was applied to drive them electrophoretically towards the nanopore sensing zone.

Figures 5A, 5B, 5C, 5D:
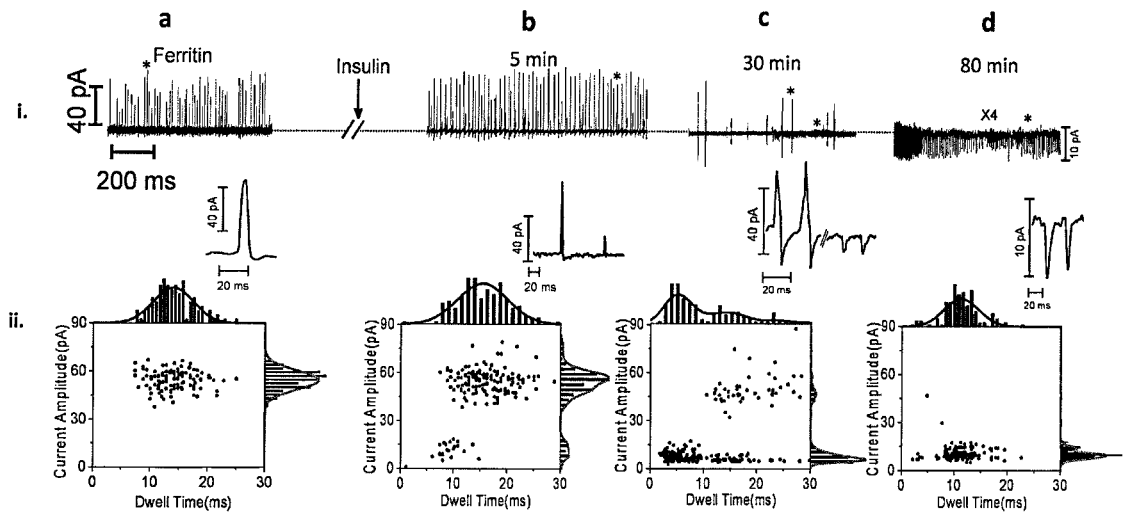
FIGS. 5A-5D. Simultaneous detection of ferritin and insulin with the nanopipette assisted fibrin hydrogel with the protein in cis side and hydrogel on the trans side. Each event is characterized by current amplitude and duration. (5A)(i) I-t traces for 500 pM ferritin in 1×PBS at −30 mV bias. Zoomed in trace of individual event is presented just below the current trace. Here, negative bias was applied, and negative current as indicated by negative current baseline was taken for measurement. (ii) The scatter plot of the current amplitude (y-axis) vs. the dwell time(y-axis) of the current spikes (n=145). (5B)(i) The i-t trace of mixture of ferritin and insulin about 5 min after the measurement. The zoomed in trace of typical two types of events. (ii) Marginal scatter plot of the current amplitude and current duration of the current spike, n=150. (5C)(i) The i-t trace recorded at 30 min after the measurement. Zoomed in traces of individual events in two different set of population presented below the current trace. (ii) The corresponding scatter plot of current amplitude vs. dwell time, (n=167). (5D)(i) The i-t trace after 80 min of recording. (ii) The scatter plot of all the current spikes showing single set of population, (n=155).

Initially, continuous upward current spikes were observed in the I-t trace at −30 mV, as shown in FIG. 5A(i). The upward current spike was due to the blocking events (resistive events) of individual translocating ferritins. The amplitude of current spikes was mostly in the range of 40-60 pA (see FIG. 5A(ii)). The uniform distribution in the scatter plot demonstrated the single set of ferritin.

The ferritin solution in the nanopore barrel was then replaced by a solution containing a mixture of ferritin and insulin both with 250 PM concentration. The loaded nanopipette was left at room temperature for about an hour. FIG. 5B (i) shows the i-t trace after applying −30 mV for 5 min. In addition to the similar type of current peaks shown in FIG. 5A(i), small upward peaks also appeared, as illustrated in the inset in FIG. 5B(i). Two sets of data points can be clearly distinguished in the scatter plot, indicating two different population of proteins, FIG. 5B(i). The distribution of the bigger peaks is very similar to the result of Ferritin alone, FIG. 5A(ii). These data can be described as Ferritin. The small peaks with the magnitude in the range of 5-20 pA were attributed to insulin. In the ionic current-time trace (FIG. 5B(i)) the ferritin peaks dominated the recorded signals with nearly 86% which is attributed to the residual ferritins from the firstly loaded ferritin alone. Currently, the insulin from the second mixed loading just reaches the tip due to higher mobility and began to show up in the recordings.

FIG. 5C(i) shows the i-t trace taken after adding the ferritin and insulin mixture for min with $V_{pore}$ at −30 mV. Two types of current spikes still appeared in the i-t trace. Now there are only a few large spikes (~25%) with the amplitude primarily (40-60) pA but a large number (~75%) of small spikes (~10-20 pA). Interestingly, the larger peaks turned out to be slightly biphasic and the small spike bounced down (conductive events). The shape changes of the spikes indicate the decrease of local ion concentration and the enhanced ion polarization due to the increased local crowding of proteins.

In the scatter plot in FIG. 5C(ii), the number of small spikes is much bigger than the number of big spikes. Therefore, the smaller insulin with the higher mobility gradually replaces the bigger ferritin at the tip. The dwell times of the translocating insulin spread out significantly. This is attributed to the increased crowding at the tip, which slows down the motion of some insulin. FIG. 5D(i) shows the i-t trace taken at nearly 80 min after the initial recording. The ionic current spikes were almost all downward small spikes due to conductive events. Accordingly, only one set of data from insulin appeared in the scatter plot (see FIG. 5d(ii)) with high even rate. There is a nearly 10% decrease in the magnitude of the current baseline. All these changes suggest at this time the insulin has fully replaced the ferritin and increased accumulation of insulin happens near the tip.

Control experiments with insulin only have also been conducted. The insulin can only be detected when the nanopore size of nanopipette is less than 20 nm with the pore/protein size ratio less than 10. If the size ratio is bigger than 10, the insulin cannot be enriched at the tip. Therefore, the ferritin plays an important role to occupy the space and promote the crowding of insulin.

Example 5—Probing Intermolecular Interactions Between Small Molecules in the Crowded Environment To demonstrate the capability of this approach for probing intermolecular interactions involving small molecules, small biomolecules ATP and GTP, which are abundant in the human body and play important functions, were studied. The GTPs can also interact with each other through Hoogsteen hydrogen bonds. In contrast, the interaction between ATP itself is much weaker.

At the beginning of the experiment, a solution of 100 pM ATP in 1×PBS is loaded inside the nanopipette with the nanopore size ~10-12 nm. As shown in the i-t trace in FIG. 6A(i), dense current spikes can be observed at −30 mV $V_{pore}$. As shown in the zoom-in, the current spike has the biphasic shape, containing a downward conductive peak followed by a resistive upward peak. Both the high current spike density and the biphasic spike shape reveal the accumulation of ATP at the tip. Then, 100 pM dTTP were added inside the nanopipette. The typical i-t trace (ii) of FIG. 6A at −30 mV bias was recorded about 20-25 min after adding dTTP solution. The accumulation was generally bigger than the case with ATP only. Interestingly, the individual spikes typically consist of two downward conductive peaks (with similar current amplitude) followed by a bigger upward resistive peak. About 70-% of the current spikes had two downward current peaks indicating that the hydrogen-bonded ATP-dTTP base pairs were formed when mixed in nanoconfined space.

Figures 6A, 6B, 6C:
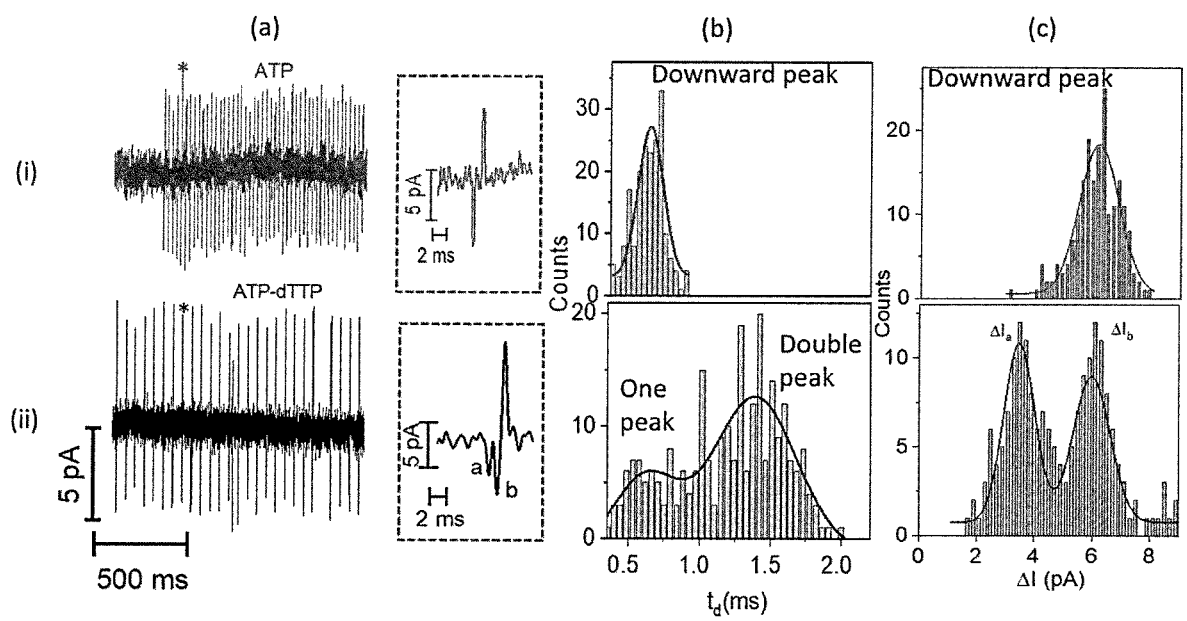
FIGS. 6A-6C. ATP-dTTP interaction through strong hydrogen bond in nano-confined region at −30 mV Vpore. (6A) The typical i-t traces of ATP (i) and ATP-dTTP complex (ii). The zoom-in of one spike is shown at the right side. (6B) (i) Histogram of dwell time of downward enhanced phase of current spike, n=191 (ii) Histogram of dwell time for enhanced downward phase of events when dTTP was added to ATP, n=212. (6C) (i) Histogram of current amplitude for downward phase of current spike with ATP alone. (ii) Histogram of current amplitude for downward current phase of ATP with dTTP.

To gain better understanding of the results, statistical analysis of the current spikes was conducted. The downward conductive peaks for both ATP and ATP-dTTP (ATP with dTTP) cases were first investigated. As shown in FIG. 6B, the histogram of dwell time of downward current spike in ATP showed unifoiin distribution with the mean dwell time of 0.6±0.3 ms. However, the histogram of ATP-dTTP shows two peaks with the first peak of 0.5±0.3 ms and the second peak of 1.4±0.6 ms. The first peak is mainly from single downward peak signals and the second peak is mainly than the double downward peak signals. The current amplitude of downward peaks was also analyzed. The histograms of current amplitude of downward current peak of ATP and ATP-dTTP are shown in FIG. 6C. The mean value of ATP (i) was at (6.5±1.6) pA and the distribution of ATP-dTTP was also much broader. Two well-distinguished peaks were observed when plotted in histogram with smaller peak of amplitude 3.5±0.5 pA and bigger peak with (5.9±0.7) pA. The observation of two downward current peaks was attributed to closely bonded ATP-dTTP complex. To corroborate bonding between ATP with dTTP, upward current amplitude between ATP and ATP-dTTP was further compared and the result showed that upward current spike of ATP-dTTP has wider distribution of current amplitude. The obvious different characteristics of the upward spikes can be attributed to the bigger size of the ATP-dTTP complex.

GTP was then measured at different V p ore using nanopipettes with similar nanopore size to the ones used in ATP measurements. One result is shown in FIG. 7A(i). When the negative $V_{pore}$ was increased to −20 mV, small clusters of biphasic current spikes appeared (see FIG. 7A(ii)). About 80-90% of the formed clusters always contain 4 biphasic current spikes, as shown in FIG. 7B(ii). These clusters can be attributed as the G-quartet complex. The G-quartet is formed through hydrogen bonding and is further stabilized by centrally coordinated mono- and divalent metal ion. The $V_{pore}$ was further increased to −40 mV. With the higher magnitude of $V_{pore}$, the event rate of the current spikes became higher and sometimes it is difficult to distinguish individual spikes (see FIG. 7A(iii)). The current spikes also became downward spikes, which is the conductive events and suggested the increased local concentration of GTP at the tip. As shown in the FIG. 7B(iii), there are two types of current spikes, fasts (28%) and slow events (72%) which is the clear indication of easy GTP aggregation at higher bias. The fast events are from individual GTPs, and the slow events are from individual GTP complexes such as G-quartet.

The $V_{pore}$ has an obvious effect on the ionic current signals of GTP translocation, reflecting its effectiveness in regulating the degree of crowding of local environment and thus the interactions between GTPs. With the increase of $V_{pore}$ magnitude, the shape of the current spikes changed from resistive upward event at lower bias (0 mV) to biphasic event and then to the conductive downward event at higher negative bias (−40 mV), indicating the increased crowding of GTP and depletion of ion concentration at the tip. Meanwhile, the interactions between GTP molecules are enhanced with the increase of crowding, leading to the formation of small complexes, including the G-quartet.

To evaluate the interactions between GTP molecules inside individual GTP complexes, the event interval($t_{int}$) between individual current spikes and the event rate were analyzed at a different bias. A significantly increased event rate and decreased time interval between spikes were observed with the increase of $V_{pore}$ magnitude (see FIG. 7C). In contrast to what has been observed at zero bias and −40 mV, two different populations of interval time at 20 mV bias were observed. The one set of data with separation ($T_{cm}$) ~6.5 ms was attributed to the time interval between GTPs inside a G-quartet whereas the other set of data ($T_{cl}$) with 120 ms was attributed to the time interval between GTP complexes.

The dwell time of GTP spikes at different $V_{pore}$ was plotted in FIG. 7D. At −20 mV, the mean duration time ($t_d$) of individual GTP spikes is 3.0±0.7 ms. The duration time was also analyzed for the G-quartet complexes ($T_{dc}$), which is 26.7±2.0 ms. Also, the dwell time distributions for the spikes at −40 mV bias was observed to be two groups corresponding to the slow and fast events shown in FIG. 7B(iii). The fast event is attributed to individual GTPs, and the slow event is attributed to a GTP complex. The continuous drop of dwell time for individual GTP and the GTP complex with the increase of $V_{pore}$ was observed.

Figure 8G:
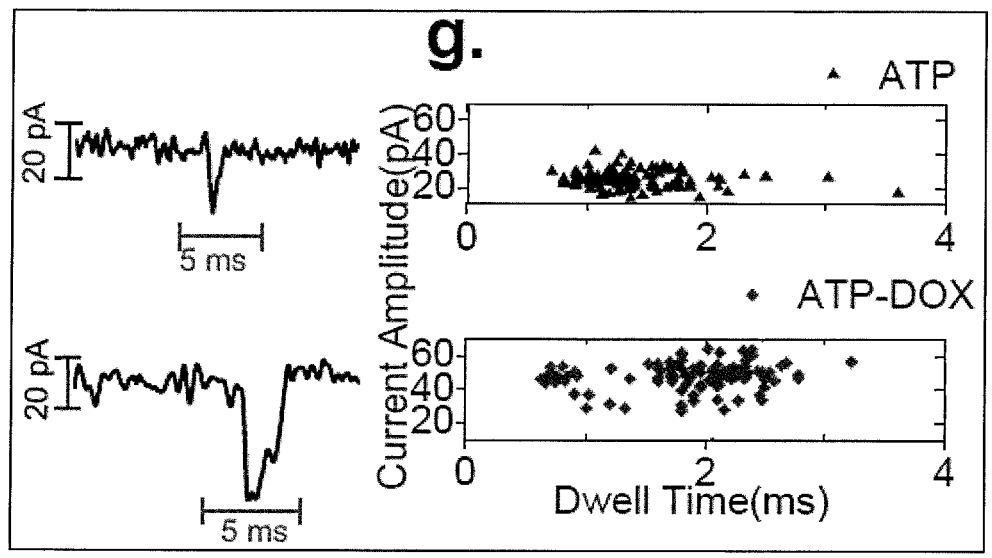
Figure 9:
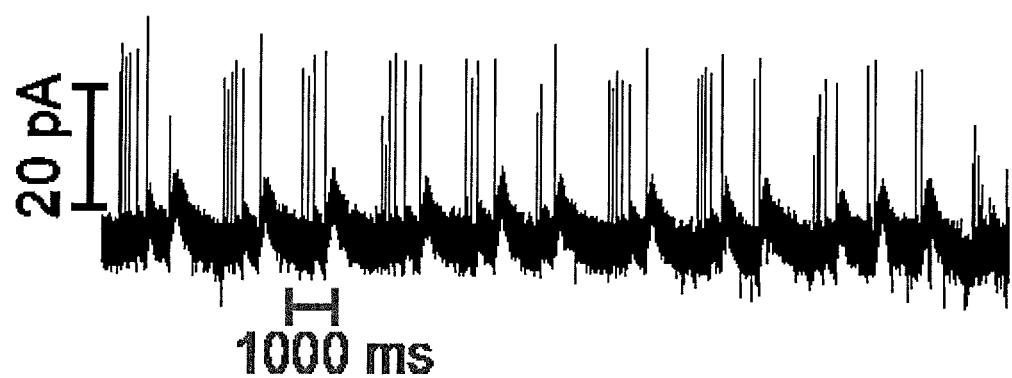
FIG. 9. Intermolecular interaction within lysozyme molecules forming oligomer.

Further, the interaction between ATP and drug molecule doxorubicin was studied. FIG. 8 shows the increased duration $t_D$ and amplitude $\Delta I$ of current spikes after mixing ATP with doxorubicin, which is attributed to the formation of ATP-doxorubicin complex. The complex is formed through intermolecular interaction between ATP and doxorubicin, which is mainly due to pi-pi stacking. Lysozyme was used as the model protein to study protein aggregation. FIG. 9 is the recorded I-t trace of positively charged (at pH 7) lysozyme protein with the size of ~14 kDa. Each upward current spike is due to the transient blockage of current by individual translocating lysozyme protein. The current spikes form clusters with different spike numbers, which revealing the formation of lysozyme oligomers.

The intermolecular interaction between biomolecules is very important and complex. The interactions present in all living beings in terms of different biological processes such as DNA replication, DNA transcriptions, and catalytic metabolism. These intermolecular interactions often happen in a confined and crowded environment. The conically shaped nanopipette tip with long taper as a nanoreactor provides an ideal reaction space with strong nanoconfinement. Due to the crowded space and the external electric force, the molecules can interact with themselves by overcoming the electrostatic repulsion and steric hindrance. Using this method, the intermolecular interaction (such as protein-protein interaction, binding interaction) and the stereochemical information of the formed molecular complex can be probed by counting the number of current spikes in each cluster.

In summary, the nanopipette nanopore can reach unprecedented sensitivity by maximizing the nano-confinement effect of nanopipette. The biomolecules can be effectively enriched at the tip after hindering their exits using fibrin hydrogel. This process is especially beneficial for the detection of small biomolecules. The dramatic concentration changes of enriched biomolecules at the tip also induce rich changes in the ionic current signals and lead to high SNR. The nanopipette can also be used as a nano-reactor to probe intermolecular interactions between small biomolecules in a crowded environment. This is an important development for the nanopipette sensor. The approach is relatively simple, inexpensive and requires no further modification. The nanopipette nanopore can be used as a portable label-free sensor for single-molecule biosensing in the point-of-care setting.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A system for enhanced single molecule detection, the system comprising a nanopipette disposed with an electrode; a crowding agent placed outside of the nanopipette to induce self-crowding of molecules inside the tip of the nanopipette; and a reference electrode placed in the crowding agent, the crowding agent being fibrin.

2. A method for enhanced single molecule detection in a sample, comprising contacting the sample with the system of claim 1; and measuring an electrical signal due to translocation of individual molecules through a nanopore of the nanopipette.

3. The method of claim 2, contacting the sample with the system comprising introducing the sample in an open barrel of the nanopipette.

4. The system of claim 1, the nanopipette being a single, double, or multi-barreled nanopipette.

5. The method of claim 2, the molecule being a protein, a peptide, a drug, or a nucleotide.

6. The method of claim 2, further comprising applying a bias in the system.

7. The method of claim 2, the nanopore having a diameter from about 10 to 90 nm.

8. A method for detecting intermolecular interactions between small biomolecules, the method comprising introducing a sample solution containing the small biomolecules into an open barrel of a nanopipette, the nanopipette having a nanopore at the tip and a working electrode disposed within the sample solution containing the small biomolecules; dipping the tip of the nanopipette in a hydrogel; placing a reference electrode in the hydrogel; and measuring an electrical signal.

9. The method of claim 8, further comprising applying a bias between the working electrode and the reference electrode.

10. The method of claim 8, the hydrogel being an ion and small molecule permeable hydrogel.

11. The method of claim 8, the hydrogel being fibrin.

12. The method of claim 8, the nanopipette being a single, double, or multi-barreled nanopipette.

13. The method of claim 8, the small biomolecules being proteins, peptides, drugs, and/or nucleotides.

14. The method of claim 8, the nanopore having a diameter from about 10 to 90 nm.

15. A method for slowing down the translocation of small biomolecules through the nanopore of a nanopipette, the method comprising introducing a sample solution containing the small biomolecules into an open barrel of a nanopipette, the nanopipette having a nanopore at the tip and a working electrode disposed within the sample solution containing the small biomolecules; dipping the tip of the nanopipette in a fibrin hydrogel; placing a reference electrode in the fibrin hydrogel; and measuring an electrical signal upon translocation of the small biomolecules through the nanopore of the nanopipette.

16. The method of claim 15, the small biomolecules being selected from ATP, ADP, AMP, GTP, GDP, GMP, microperoxidase-11 (MP-11), nisin, cytochrome-c, insulin, high-mobility group AT-hook 2 (HMGA2), and lysozyme.

17. The method of claim 15, the nanopore having a diameter from about 10 to 90 nm.

18. The method of claim 15, the nanopipette being a single or double barreled nanopipette.

19. The method of claim 15, the small biomolecules being proteins, peptides, drugs, and/or nucleotides.

* * * * *